United States Patent
Kåss

(10) Patent No.: US 10,821,152 B2
(45) Date of Patent: *Nov. 3, 2020

(54) METHODS, AGENTS AND COMPOSITIONS FOR TREATMENT OF INFLAMMATORY CONDITIONS

(71) Applicant: Betanien Hospital, Skien (NO)

(72) Inventor: Anita Kåss, Porsgrunn (NO)

(73) Assignee: BETANIEN HOSPITAL, Skein (NO)

( * ) Notice: Subject to any disclaimer, the term of this patent is extended or adjusted under 35 U.S.C. 154(b) by 120 days.

This patent is subject to a terminal disclaimer.

(21) Appl. No.: 15/506,210

(22) PCT Filed: Aug. 24, 2015

(86) PCT No.: PCT/EP2015/069369
§ 371 (c)(1),
(2) Date: Feb. 23, 2017

(87) PCT Pub. No.: WO2016/030334
PCT Pub. Date: Mar. 3, 2016

(65) Prior Publication Data
US 2017/0258867 A1    Sep. 14, 2017

Related U.S. Application Data

(60) Provisional application No. 62/041,873, filed on Aug. 26, 2014, provisional application No. 62/082,200, filed on Nov. 20, 2014, provisional application No. 62/110,731, filed on Feb. 2, 2015, provisional application No. 62/181,289, filed on Jun. 18, 2015.

(51) Int. Cl.

| | | |
|---|---|---|
| *A61K 38/09* | (2006.01) | |
| *A61K 45/06* | (2006.01) | |
| *A61K 31/568* | (2006.01) | |
| *A61K 31/565* | (2006.01) | |
| *A61K 47/60* | (2017.01) | |
| *A61K 31/4184* | (2006.01) | |
| *A61K 31/4409* | (2006.01) | |
| *A61K 31/519* | (2006.01) | |
| *G01N 33/74* | (2006.01) | |
| *A61K 9/00* | (2006.01) | |
| *A61K 31/513* | (2006.01) | |
| *A61K 31/58* | (2006.01) | |
| *A61K 39/395* | (2006.01) | |
| *C07K 16/28* | (2006.01) | |
| *G01N 33/564* | (2006.01) | |
| *A61K 39/00* | (2006.01) | |

(52) U.S. Cl.
CPC ............ *A61K 38/09* (2013.01); *A61K 9/0019* (2013.01); *A61K 9/0053* (2013.01); *A61K 31/4184* (2013.01); *A61K 31/4409* (2013.01); *A61K 31/513* (2013.01); *A61K 31/519* (2013.01); *A61K 31/565* (2013.01); *A61K 31/568* (2013.01); *A61K 31/58* (2013.01); *A61K 39/3955* (2013.01); *A61K 45/06* (2013.01); *A61K 47/60* (2017.08); *C07K 16/2869* (2013.01); *G01N 33/564* (2013.01); *G01N 33/74* (2013.01); *A61K 2039/505* (2013.01); *C07K 2317/76* (2013.01); *G01N 2333/575* (2013.01); *G01N 2800/065* (2013.01); *G01N 2800/10* (2013.01); *G01N 2800/102* (2013.01); *G01N 2800/205* (2013.01); *G01N 2800/285* (2013.01); *G01N 2800/7042* (2013.01); *G01N 2800/7095* (2013.01)

(58) Field of Classification Search
None
See application file for complete search history.

(56) References Cited

U.S. PATENT DOCUMENTS

| | | |
|---|---|---|
| 6,346,534 B1 | 2/2002 | Zhu et al. |
| 7,569,688 B2 | 8/2009 | Hirano et al. |
| 8,076,367 B2 | 12/2011 | Hirano et al. |
| 2003/0045475 A1 | 3/2003 | Jacobson |
| 2003/0144203 A1 | 7/2003 | Bowen |
| 2004/0087565 A1 | 5/2004 | Kosemund et al. |
| 2004/0138138 A1 | 7/2004 | Engel et al. |
| 2004/0142942 A1 | 7/2004 | Zhu et al. |
| 2004/0265285 A1 | 12/2004 | Boyd |

(Continued)

FOREIGN PATENT DOCUMENTS

| | | |
|---|---|---|
| EP | 2505204 A2 | 10/2012 |
| JP | 2007-325581 A | 12/2007 |

(Continued)

OTHER PUBLICATIONS

Australian Governement: Dept of Health and Aging (Australian Public Assessment Report for Degarelix; May 2010).*

(Continued)

*Primary Examiner* — James H Alstrum-Acevedo
*Assistant Examiner* — Tara L Martinez
(74) *Attorney, Agent, or Firm* — Porter Wright Morris & Arthur LLP

(57) ABSTRACT

The present invention relates to the screening, diagnosis, prognostic evaluation, and treatment or prevention of age associated inflammation, chronic inflammation, and inflammatory diseases. In particular, the present invention relates to treating or preventing inflammatory diseases (e.g. rheumatoid arthritis or spondyloarthritis) or patients with inflammatory peripheral GnRH with GnRH antagonists or drugs that lower the effects of GnRH.

11 Claims, 19 Drawing Sheets

(56) References Cited

U.S. PATENT DOCUMENTS

| | | | |
|---|---|---|---|
| 2006/0287282 | A1 | 12/2006 | Steiner et al. |
| 2010/0092463 | A1 | 4/2010 | Ishikawa et al. |
| 2011/0218210 | A1 | 9/2011 | Refaeli et al. |
| 2014/0113870 | A1 | 4/2014 | Olesen et al. |

FOREIGN PATENT DOCUMENTS

| | | | |
|---|---|---|---|
| WO | 97/21435 | A1 | 6/1997 |
| WO | 97/21704 | A1 | 6/1997 |
| WO | 97/44037 | A1 | 11/1997 |
| WO | 97/44321 | A1 | 11/1997 |
| WO | 97/44339 | A1 | 11/1997 |
| WO | 98/55116 | A1 | 12/1998 |
| WO | 98/55470 | A1 | 12/1998 |
| WO | 98/55479 | A1 | 12/1998 |
| WO | 02/11732 | A1 | 2/2002 |
| WO | 03/011314 | A2 | 2/2003 |
| WO | 03/104253 | A2 | 12/2003 |
| WO | 2005/005443 | A1 | 1/2005 |
| WO | 2005/007165 | A1 | 1/2005 |
| WO | 2006/064263 | A1 | 6/2006 |
| WO | 2006/064277 | A1 | 6/2006 |
| WO | 2007/000582 | A1 | 1/2007 |
| WO | 2009/106597 | A1 | 9/2009 |
| WO | WO 2010/033207 | * | 3/2010 |
| WO | 2011/076687 | A1 | 6/2011 |
| WO | 2011/144756 | A1 | 11/2011 |
| WO | 2012/175514 | A1 | 12/2012 |
| WO | 2014/104791 | A1 | 7/2014 |

OTHER PUBLICATIONS

Merck Manual (https://www.merckmanuals.com/professional/musculoskeletal-and-connective-tissue-disorders/joint-disorders/rheumatoid-arthritis-ra> accessed Feb. 2, 2019).*

The Merck Manual (https://www.merckmanuals.com/professional/neurologic-disorders/demyelinating-disorders/multiple-sclerosis-ms accessed Feb. 2, 2019).*

Rick et al. ("LHRH antagonist Cetrorelix reduces prostate size and gene expression of proinflammatory cytokines and growth factors in a rat model of benign prostatic hyperplasia"; The Prostate 71:736-747(2011)).*

Cutulo ("Sex hormone adjuvant therapy in rheumatoid arthritis" Rheum Dis Clin AM 2000; 26(4) 881-95).*

Kass et al. (Cetrorelix, a Gonadotropin-releasing hormone, reduces disease activity and tumor necrosis factor-alpha in rheumatoid arthritis: A proof of concept, double blind, parallel group randomized controlled trial (AGRA Trial) ; The Endocrine Society's 94th Annual Meeting and Expo, presented Jun. 23, 2012).*

Sifasi HP (Feb. 2001, seruminstitute.com).*

Cutulo ("Sex hormone adjuvant therapy in rheumatoid arthritis" Rheum Dis Clin AM 2000; 26(4) 881-95, previously cited).*

Ansari, M. A. et al., Modulation of Diabetes with Gonadotropin-Releasing Hormone Antagonists in the Nonobese Mouse Model of Autoimmune Diabetes, Endocrinology, 145(1): 337-342 (2004).

Macewan, D. J., Interactions Between TNF and GnRH, Neurochemical Research, 33:678-682 (online Nov. 6, 2007).

Michel, L. et al., Increased Risk of Multiple Sclerosis Relapse After in vitro Fertilisation, J Neurol Neurosurg Psychiatry, 83: 796-802 (online Jun. 11, 2012).

Kåss, A. et al., Cetrorelix, a Gonadotropin-Releasing Hormone Antagonist, Significantly Reduces Tumour-Necrosis-Factor-Alpha and Demonstrates Efficacy in Patients with Active Rheumatoid Arthritis: A Proof-of-Concept, Double-Blind, Randomised Trial, Arthritis & Rheumatism, 64(10): S363-S364, Abstract No. 834 (2012).

Kåss, A. et al., Cetrorelix, a Gonadotropin-Releasing Hormone Antagonist, in Rheumatoid Arthritis, Presentation, 76th Annual Meeting of the American College of Rheumatology, Washington D.C. (2012).

Smith, M. R. et al., Gonadotropin-Releasing Hormone Blockers and Cardiovascular Disease Risk: Analyses of Prespective Clinical Trials of Degarelix, Journal of Urology, 186(5): 1835-1842 (Nov. 2011).

Duivenvoorden, W. C. M. et al., GnRH Antagonists Associate with Less Weight Gain and Milder Characteristics of the Metabolic Syndrome and Atherosclerosis Compared to Surgical Castration and GnRH Analogues in Pre-Clinical Animal Model, Journal of Urology 191(4S): e263, Abstract No. MP24-11 (May 18, 2014).

Kåss, A. et al., Cetrorelix, a Gonadotropin-Releasing Hormone Antagonist, Demonstrates Efficacy and Significantly Reduces Proinflammatory Cytokines in Patients with Active Longstanding Rheumatoid Arthritis with High Gonadotropin Levels: A Proof-of-Concept, Double-Blind, Randomized Trial, Abstract No. L12, 77th Annual Meeting of the American College of Rheumatology, San Diego CA (Oct. 2013).

Kåss, A. et al., Cetrorelix, a Gonadotropin-Releasing Hormone Antagonist, Demonstrates Efficacy and Significantly Reduces Cytokines in Patients with Active Longstanding Rheumatoid Arthritis with High Gonadotropin Levels: A Proof-of-Concept, Double-Blind, Randomised Trial, Poster No. L12, 77th Annual Meeting of the American College of Rheumatology, San Diego CA (Oct. 26, 2013).

Albertsen, P. et al., Androgen Deprivation Therapy by a Gonadotropin-Releasing Hormone Antagonist, Degarelix, Lowers the Risk of Cardiovascular Events or Death when Compared to Luteinising Hormone-Releasing Agonists, Journal of Urology, 189(4S): e322, Abstract No. 781 (May 6, 2013).

Jacobson, J. D. et al., Modulation of the Expression of Murine Lupus by Gonadotropin-Releasing Hormone Analogs, Endocrinology, 134(6): 2516-2523 (1994).

Kåss, A. et al., The Association of Luteinizing Hormone and Follicle-Stimulating Hormone with Cytokines and Markers of Disease Activity in Rheumatoid Arthritis: A Case-Control Study, Scandinavian Journal of Rheumatology, 39(2): 109-117 (2010).

Kåss, A. et al., Short-Term Treatment with a Gonadotropin-Releasing Hormone Antagonist, Cetrorelix, in Rheumatoid Arthritis (AGRA): A Randomised, Double-Blind, Placebo-Controlled Study, Scandinavian Journal of Rheumatology, 43(1):22-27 (2014).

Kåss, A. et al., Cetrorelix, a Gonadotropin-Releasing Hormone Antagonist, Significantly Reduces TNF-alpha and Demonstrates Efficacy in Patients with Active Rheumatoid Arthritis: A Proof-of-Concept, Double-Blind Randomised Trial, Annals of the Rheumatic Diseases, 71(Suppl. 3) 123, Abstract OP0202 (2012).

Wen, J. et al., Luteinizing Hormone-Releasing Hormone (LHRH)-I Antagonist Cetrorelix Inhibits Myeloma Cell Growth in vitro andin vivo, Molecular Cancer Therapeutics, 10(1): 148-158 (2010).

Clyne, M., Cardiovascular Morbidity Risk Lower for ADT with GnRH Antagonists than GnRH Agonists, Nature Reviews Urology, 10: 679 (online Nov. 19, 2013).

Von Dehn, G. et al., Atherosclerosis in Apolipoprotein E-Deficient Mice is Decreased by the Suppression of Endogenous Sex Hormones, Hormone and Metabolic Research, 33(2): 110-114 (2001).

Albertsen, P.C. et al., Cardiovascular Morbidity Associated with Gonadotropin Releasing Hormone Agonists and an Antagonist, European Urology, 65(3): 565-573 (Nov. 1, 2013).

Rick, F. G. et al., LHRH Antagonist Cetrorelix Reduces Prostate Size and Gene Expression of Proinflammatory Cytokines and Growth Factors in a Rat Model of Benign Prostatic Hyperplasia, The Prostate, 71(7):736-747 (online Oct. 14, 2010).

Rosario, D. J. et al., Androgen Deprivation Therapy and Cardiovascular Harm: Are All Men Created Equal?, European Urology, 65(3): 574-576 (Nov. 20, 2013).

Yanagita, Y. & Takenaka, T., Astellas' Drug Discovery Strategy: Focus on Oncology, Japanese Journal of Clinical Oncology, 42(4): 241-246 (2012).

Sifasi-HP (Cetrorelix) Safety Sheet, Serum Institute of India Ltd., Pune, India (2001).

Firmagon Product Information, Annexes to EU Marketing Authorisation EU/1/08/504/001, European Medicines Agency, London UK (2008).

Gonadotropin-Releasing Hormone (GnRH)-Antagonist Therapy in Rheumatoid Arthritis (AGRA), Clinical Trial Summary, ClinicalTrials.gov, U.S. National Institutes of Health (2012).

(56) References Cited

OTHER PUBLICATIONS

Official Action dated Sep. 4, 2019 from corresponding European Application No. 15756614.2.
Official Action from corresponding Japanese Application No. 2017-530419 dated Jul. 16, 2019 and English Translation.
Broqua, Pierre et al., Pharmacological Profile of a New, Potent, and Long-Acting Gonadotropin-Releasing Hormone Antagonist: Degarelix, The Journal of Pharmacology and Experimental Therapeutics, vol. 301, No. 1, pp. 95-102 (2002).
Koechling, Wolfgang et al., Degarelix, a novel GnRH antagonist, causes minimal histamine release compared with cetrorelix, abarelix and ganirelix in an ex vivo model of human skin samples, British Journal of Clinical Pharmacology, vol. 70, No. 4, pp. 580-587 (2010).
Sbracia, M. et al., Use of Depot GnRH Antagonist (Degarelix) in The Ovarian Stimulation in Women With PCOS Undergoing IVF. A Controlled Trial, Fertility & Sterility, pp. S1 (Oct. 22, 2012).
Official Action dated May 8, 2020 from corresponding European Application No. 15756614.2.
Examination Report No. 1 dated May 25, 2020 from corresponding Australian Application No. 2015308987.

* cited by examiner

Fig. 1A: Before Degarelix
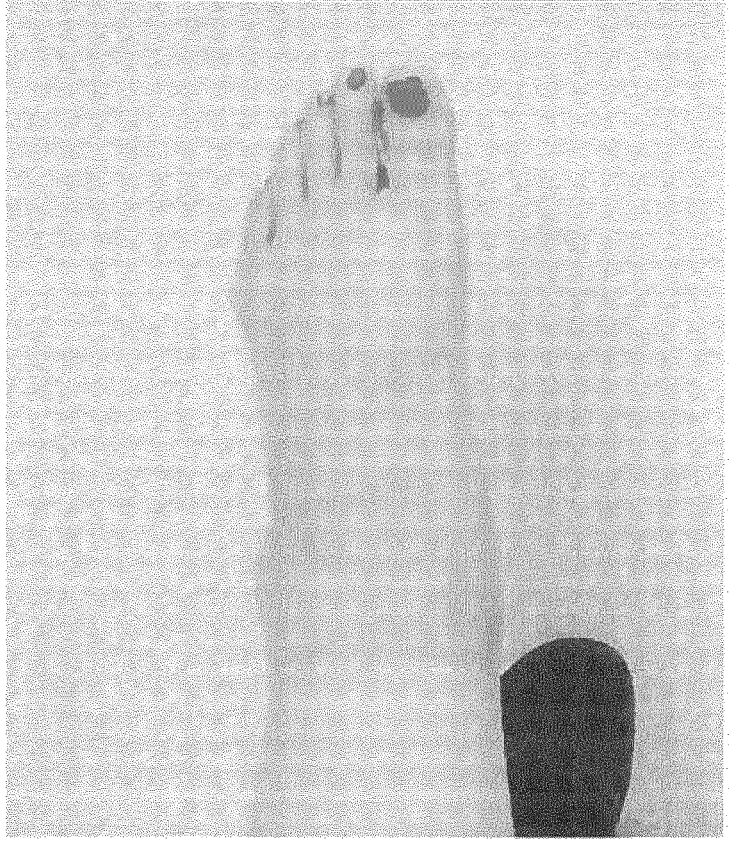
Fig. 1B: After Degarelix

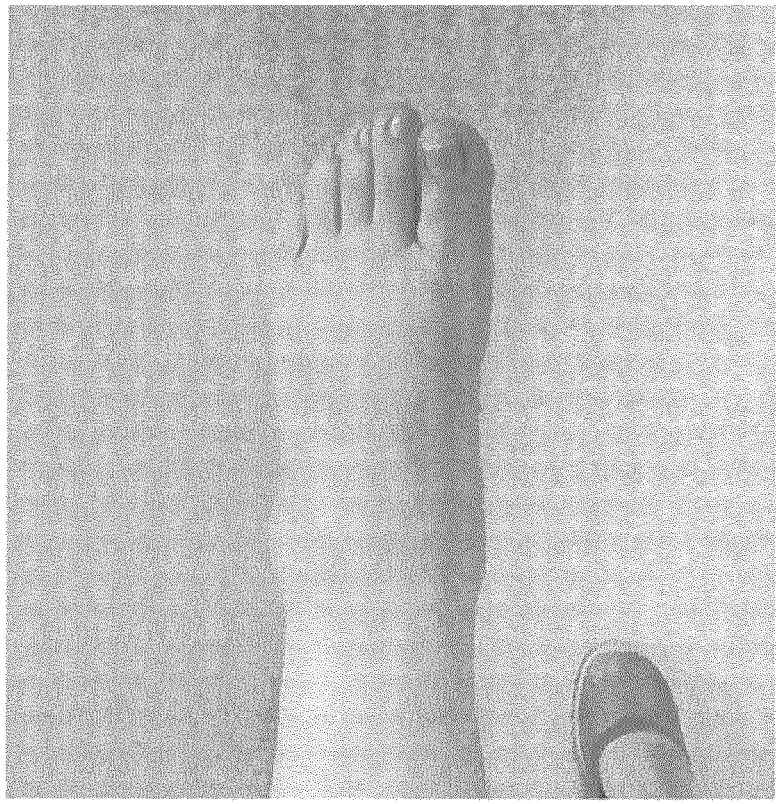
Fig. 1C: After Degarelix treatment for 5 months

AFTER: No power Doppler in shoulder

BEFORE: White area highlighted by arrow, is power Doppler denoting inflammatory activity in right MCP 4 (finger joint) right side.

AFTER: No power Doppler in MCP 4 right side.

BEFORE: White area highlighted by arrow, is power Doppler denoting inflammatory activity in right MCP 4 (finger joint) left side.

AFTER: No power Doppler in MCP 4 left side, and decreased joint fluid (oval).

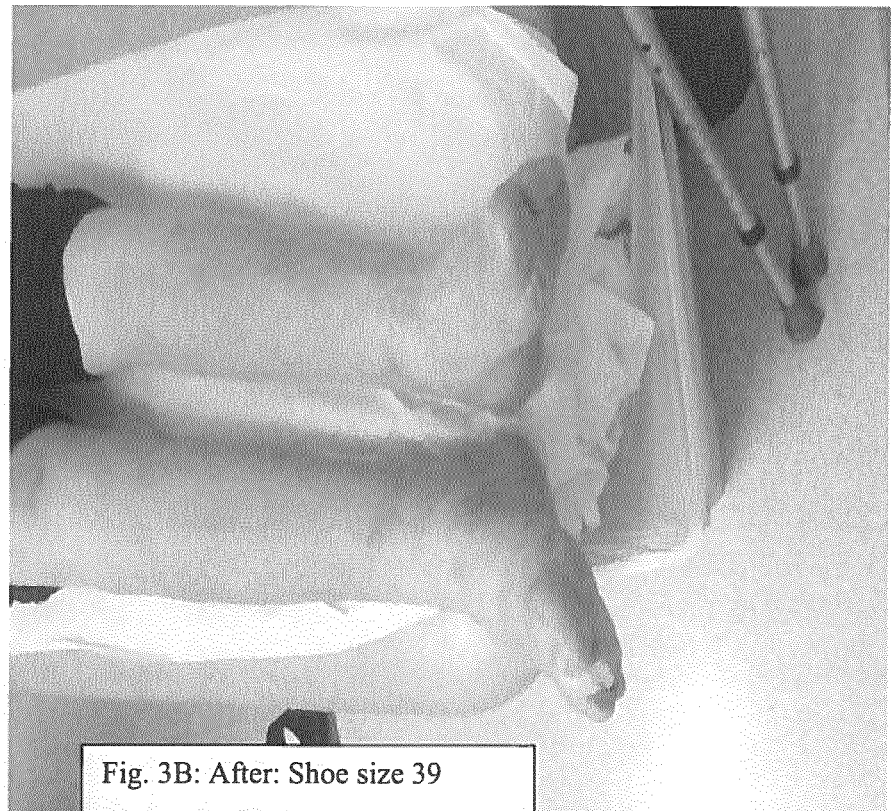
Fig. 3B: After: Shoe size 39
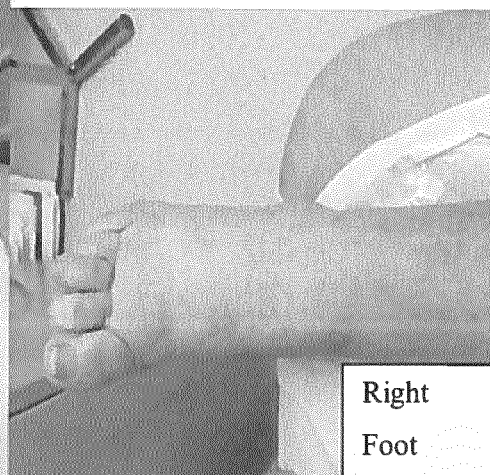
Right Foot

Fig. 4
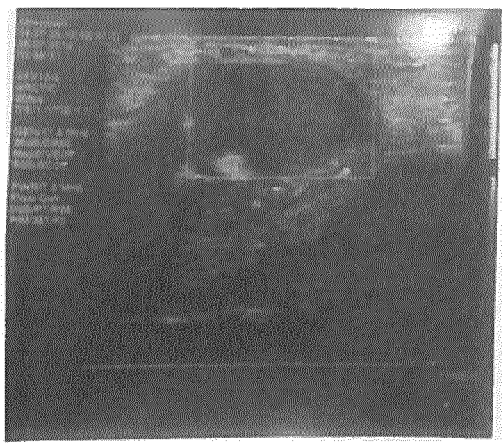 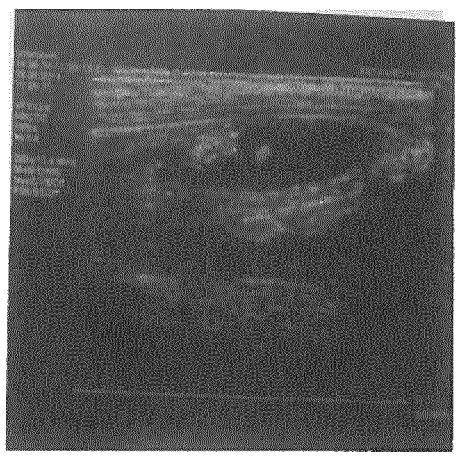

Stable 10mg/wk Methotrexate since 1999-2014: *High disease activity 7-7.3* units on avg.

GnRH Antagonist started at month 0 June '14:
*Disease activity improves by 2.2 units*

Methotrexate stopped at 3.5 Oct '14 months:
*Disease activity worsens 0.6 units*

METHODS, AGENTS AND COMPOSITIONS FOR TREATMENT OF INFLAMMATORY CONDITIONS

FIELD OF THE INVENTION

The present invention relates to the screening, diagnosis, prognostic evaluation, and treatment or prevention of age associated inflammation, chronic inflammation, and inflammatory diseases. In particular, the present invention relates to methods, agents and compositions for treating inflammatory diseases (e.g. rheumatoid arthritis or spondyloarthritis) or patients with inflammatory peripheral GnRH with GnRH antagonists, including drugs that lower the effects of GnRH or GnRH inhibitors.

BACKGROUND OF THE INVENTION

Ageing is among the largest known risk factors for human diseases. Roughly 100,000 people die each day of age-related causes. Between 2000 and 2050, the proportion of the number of people aged 60 years and over is expected to increase from 605 million to 2 billion.

Chronic inflammation is associated with normal and pathological ageing. Systemic chronic inflammation can accelerate ageing (Jurk D, et al., Nat Comm, 2014; doi: 10.1038/ncomms5172). Many age-related diseases and ageing itself are closely associated with low-level chronic inflammation (Chung H Y, et al., Ageing Res Rev 2009; 8: 18-30). Inflammatory markers are significant predictors of mortality in older humans. This pro-inflammatory status of the elderly underlies biological mechanisms responsible for the decline of physical function decline and age-related diseases such as Alzheimer's disease and atherosclerosis that are initiated or worsened by systemic inflammation. Understanding of the ageing process should have a prominent role in new strategies for extending the health of the older population.

Inflammatory diseases themselves accelerate the ageing process due to systemic chronic inflammation. Many of these diseases, such as rheumatoid arthritis and multiple sclerosis accelerate cardiovascular disease and osteoporosis, both of which are examples of age-related conditions. Indeed, inflammatory diseases have on average a 10 year premature mortality largely due to increased cardiovascular disease.

Rheumatoid arthritis is a chronic, systemic inflammatory disorder that may affect many tissues and organs, but principally attacks the joints producing an inflammatory synovitis that progresses to cartilage and bone destruction. Rheumatoid arthritis can also produce diffuse inflammation in the lungs, pericardium, pleura and sclera, and also nodular lesions, most common in subcutaneous tissue under the skin. Although the cause of rheumatoid arthritis is unknown, autoimmunity plays a role in its chronicity and progression.

About 1% of the world's population is afflicted by rheumatoid arthritis, women three times more often than men. Onset is most frequent between the ages of 40 and 50, but people of any age can be affected. It can be a disabling and painful condition which can lead to substantial loss of functioning and mobility. It is diagnosed chiefly on symptoms and signs, but also with blood tests (e.g., a test for anti-CCP antibodies) and X-rays. Diagnosis and long-term management are typically performed by a rheumatologist, an expert in the diseases of joints and connective tissues.

There is no cure for ageing, chronic inflammation or inflammatory diseases. We have improved life expectancy due to various factors, including the prevention and treatment of cardiovascular disease. Nowadays, new biologic drugs for inflammatory diseases are available. The efficacy of such drugs is still inadequate in a large proportion of patients. For example, only about two thirds of patients with rheumatoid arthritis respond at any level to currently available biologic drugs. Of these patients, a significant proportion will have to cease these treatments either due to loss of efficacy over time, or serious side effects. So the average time rheumatoid arthritis patients can use a biologic is about 2 years. Current treatments for rheumatoid arthritis include: corticosteroids, methotrexate, tumour necrosis factors inhibitors such as etanercept (Embrel®), adalimubab (Humira®), and infliximab (Remicade®), and other immunomodulatory and cytotoxic agents. Whilst these treatments can be effective many require close supervision because of hazardous side-effects. Response to treatment with these agents is variable and some patients will experience pain and joint degeneration. Thus there is a need for additional treatments for rheumatoid arthritis and related diseases. Other inflammatory diseases have no disease modifying therapies available, such as progressive multiple sclerosis.

Therefore there is a need for earlier diagnosis, improved screening and prognostic evaluation, as well as better treatment and prevention of inflammatory diseases, chronic inflammation, and age-related inflammation.

SUMMARY OF THE INVENTION

The present invention relates to the screening, diagnosis, prognostic evaluation, and treatment or prevention of inflammatory conditions including age associated inflammation, chronic inflammation, and inflammatory diseases. In particular, the present invention relates to methods of treating inflammatory diseases (e.g. rheumatoid arthritis or spondyloarthritis) or patients with inflammatory peripheral GnRH with GnRH antagonists or drugs that lower the effects of GnRH. Inflammatory conditions generally require or benefit from long term treatment.

Accordingly, a first aspect of the invention provides a GnRH antagonist for use in the treatment or prevention of an inflammatory condition in a subject, selected from an inflammatory disease, chronic inflammation, age-related inflammation or inflammatory peripheral GnRH, wherein said GnRH antagonist is for long-term administration to said subject for a period of at least 12 weeks.

Also provided according to the invention is a pharmaceutical composition comprising a GnRH antagonist for such use, together with at least one pharmaceutically acceptable carrier or excipient. Thus, this aspect of the invention provides a pharmaceutical composition comprising a GnRH antagonist for use in the treatment or prevention of an inflammatory condition in a subject, selected from an inflammatory disease, chronic inflammation, age-related inflammation or inflammatory peripheral GnRH, wherein said composition is for long-term administration to said subject for a period of at least 12 weeks.

In a further aspect, the invention provides use of a GnRH antagonist for the manufacture of a medicament for use in the treatment or prevention of an inflammatory condition in a subject, selected from an inflammatory disease, chronic inflammation, age-related inflammation or inflammatory peripheral GnRH, wherein said GnRH antagonist is for long-term administration to said subject for a period of at least 12 weeks.

In a still further aspect, the invention also provides a method of treating or preventing an inflammatory condition in a subject, selected from an inflammatory disease, chronic inflammation, age-related inflammation or inflammatory peripheral GnRH, said method comprising administering a GnRH antagonist to said subject, wherein said GnRH antagonist is administered long-term to said subject for a period of at least 12 weeks.

Embodiments of the present invention provide methods, and uses based thereon, for the screening, diagnosis, prognostic evaluation, and treatment or prevention of age associated inflammation, chronic inflammation, inflammatory peripheral GnRH and inflammatory diseases, comprising administering a GnRH antagonist to the subject, as well as agents and compositions for such treatment. The present invention is not limited to a particular inflammatory disease. Examples include, but are not limited to, rheumatoid arthritis, multiple sclerosis, systemic lupus erythematosus, ankylosing spondylitis, spondyloarthritis, psoriasis, systemic sclerosis (scleroderma), inflammatory bowel disease, multiple sclerosis, osteoarthritis and other forms of arthritis (e.g. psoriatic arthritis) and nephritis. In one embodiment the inflammatory conditions do not include systemic lupus erythematosus.

Patients with peripheral GnRH include, but are not limited to, those with age associated inflammation, chronic inflammation, autoimmune disease, cardiovascular disease, osteoporosis, Alzheimer's disease, cataracts, cancers, cancer associated inflammation, postpartum and gonadal failure (including natural and surgical menopause, polycystic ovarian syndrome and Turner's syndrome). As will be described in more detail below, subjects with peripheral GnRH do not necessarily have an inflammatory disease and may be healthy. "Peripheral GnRH" and more particularly "inflammatory peripheral GnRH" are defined further below.

The present invention is not limited to a particular GnRH antagonist. Examples include, but are not limited to, cetrorelix, ganirelix, abarelix, degarelix, detirelix, iturelix, ozarelix, prazarelix, ramorelix, elagolix, relugolix, ASP1707, teverelix, D17DT GnRH vaccination, or spiroindoline derivatives as gonadotropin-releasing hormone receptor antagonists. In some embodiments, the GnRH antagonist is ASP1707.

In some embodiments, the GnRH antagonist is administered in one or more repeated doses (e.g. several times daily, daily, weekly, monthly, or other interval) for a period of time. According to the invention as set out above the GnRH antagonist is administered for a period of at least 12 weeks, (e.g. at least three months, at least 6 months, at least 1 year, at least 3 years, at least 5 years, or at least 10 years, or longer). However, as discussed below, in certain further aspects of the invention the GnRH antagonist may be administered for a shorter period (e.g. at least one week, at least two weeks, at least one month, at least two months), In some embodiments, the GnRH antagonist is administered at a dose of 0.1 mg to 1000 mg (e.g. 0.1, 0.25, 0.5, 1.0, 5.0, 10, 25, 50, 100, 200, 300, 400, 500, 750, or 1000 mg) In some embodiments, the GnRH antagonist is administered multiple times per day, daily, weekly, or monthly. In some embodiments, the GnRH antagonist is administered with an initial loading dose between 20 mg to 1000 mg (e.g. 20, 30, 40, 50, 60, 100, 200, 300, 400, 500, or 1000 mg) followed by a lower maintenance dose administered multiple times per day, daily, weekly, or monthly, or at least every 2-12 months.

In some embodiments, a long acting GnRH antagonist such as Degarelix, Ozarelix or Abarelix is administered weekly, or every 2-4 week intervals, or monthly intervals or every 2-6 month intervals, or yearly, 10 mg to 1000 mg, in some embodiments, with an initial loading dose of the long acting GnRH antagonist between 20 mg to 1000 mg. Further doses and dosage regimes are discussed below.

In some embodiments, short acting GnRH antagonists, such as Cetrorelix or Ganirelix, are administered up to 6 times daily, e.g. 2, 3 or 4 to 6 times daily, or daily or 2-6 times weekly or weekly or every 2-4 weeks at a dose of 0.1 mg to 30 mg, for example 0.75 mg to 30 mg or 2 mg to 30 mg (e.g., 0.1, 0.25, 0.5, 1.0, 5.0, 10.0, 25, 30 mg).

In some embodiments, oral GnRH antagonists such as nonpeptide oral GnRH antagonists, spiroindoline derivatives as gonadotropin-releasing hormone receptor antagonists, Relugolix, Elagolix, or ASP1707 is administered up to 6 times daily, e.g. 2, 3 or 4 to 6 times daily, or daily, or 2-6 times weekly or weekly at a dose of 0.1 mg to 3 g (e.g. 0.1, 0.25, 0.5, 1.0, 5.0, 10.0, 25, 50, 100, 500, 1000, 2000 or 3000 mg).

In some embodiments, the present invention combats inflammatory or age-associated bio-markers such as TNF-α, IL-1, IL-6 or IGF-1, an amount dependent on their age and sex in the form of a medicament.

Certain embodiments provide for the treatment or prevention of osteoporosis and/or increasing bone mineral density in a subject, by administering a GnRH antagonist to the subject, or administering a GnRH antagonist, with titrated oestrogen or testosterone to baseline or higher levels, or with an osteoporosis drug.

Some embodiments provide for treating or preventing age associated inflammation, chronic inflammation or cardiovascular disease, or decreasing the risk of cardiovascular disease, or decreasing a patient's risk for developing coronary heart disease or having a cardiovascular event, including a recurrent cardiovascular event, e.g. by decreasing HBA1c or fasting blood glucose levels, decreasing blood pressure, decreasing chronic inflammation, or increasing HDL levels or decreasing LDL levels in a subject, by administering a GnRH antagonist to the subject, or administering a GnRH antagonist, with titrated oestrogen, or testosterone to baseline or higher levels, or with a drug to treat cardiovascular disease.

The present invention further provides for the use of a GnRH antagonist in the treatment of an autoimmune disease in a subject in need thereof.

Some embodiments provide for decreasing a patient's risk for developing metabolic syndrome or developing type II diabetes, including decreasing HbA1C or fasting glucose in a subject by administering a GnRH antagonist to the subject.

Additional embodiments provide for treating systemic sclerosis (scleroderma) in a subject, by administering a GnRH antagonist to the subject.

Certain embodiments provide for treating multiple sclerosis in a subject, by administering a GnRH antagonist to the subject.

Additional embodiments provide for treating inflammatory bowel disease in a subject, by administering a GnRH antagonist to the subject.

Further embodiments provide for treating psoriasis in a subject, by administering a GnRH antagonist to the subject.

In some embodiments, the present invention provides for the use of a GnRH antagonist in the treatment of ankylosing spondylitis.

In some embodiments, the present invention provides for the use of a GnRH antagonist in the treatment of spondyloarthritis.

In some embodiments, the present invention provides the use of a GnRH antagonist in the treatment of nephritis.

In some embodiments, the present invention provides the use of a GnRH antagonist in the treatment of cancer inflammation.

In other embodiments, the GnRH antagonist may be used for decreasing HBA1c, decreasing blood pressure, or increasing HDL levels in a subject.

In other embodiments, the present invention provides methods and uses of a GnRH antagonist to lower the levels of cytokines and/or chemokines in a subject. In some embodiments the proinflammatory cytokines are TNFa, IFNg, IL-1b and/or IL-2. In some embodiments, the present invention provides the use of a GnRH antagonist to lower the levels of acute phase proteins such as CRP or high sensitivity CRP or the levels of auto-antibodies such as antibodies e.g. cyclic citrullinated peptide (CCP).

Further embodiments of the present invention provide methods and uses of treating an autoimmune or inflammatory disease, comprising: a) identifying subjects that exhibit one or more of: are negative for anti-cyclic citrullinated peptide (CCP) antibodies; are non-responders to anti-TNF therapy or disease-modifying anti-rheumatic drugs (DMARDs); and b) administering a GnRH antagonist to the subjects.

In some embodiments, the present invention provides for the use of combination therapy, particularly titrated oestrogen or testosterone therapy to baseline or higher levels, or a disease modifying drug, or stable or tapered prednisolone, or local topical treatment, or a biologic drug, with a GnRH antagonist in the prevention or treatment of an inflammatory condition selected from age associated inflammation, chronic inflammation, inflammatory peripheral GnRH and inflammatory diseases.

The present invention further provides an agent, e.g. a GnRH antagonist, particularly a conjugate comprising a GnRH antagonist linked to a polymer, and pharmaceutical compositions comprising said agent, as described further herein. The present invention also provides for the use of said agents and compositions in therapy, particularly in the uses and methods described herein.

Additional embodiments will be apparent to persons skilled in the relevant art based on the teachings contained herein.

DESCRIPTION OF THE DRAWINGS

FIGS. 1A, 1B and 1C show images of arthritis in the foot of patient 1 before and during treatment with degarelix.

FIG. 2 shows ultrasound pictures of patient 5.

FIG. 3 shows patient 6 before (FIG. 3A) and after (FIG. 3B) degarelix treatment.

FIG. 4 shows ultrasounds of patient 6. The first ultrasound (left) shows a large effusion (swelling indicated by black area) over the right wrist. The second ultrasound (right) shows the same area by 3.5 weeks. The effusion on the right is much smaller, and no longer painful.

DEFINITIONS

Figure 2A:
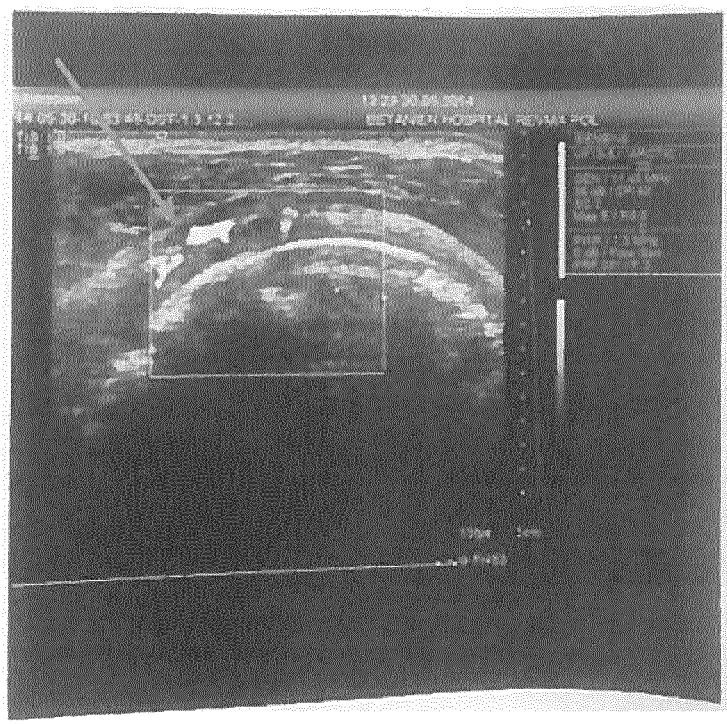
FIG. 2A shows white area highlighted by arrow, is power Doppler denoting inflammatory activity in shoulder.
Figure 2B:
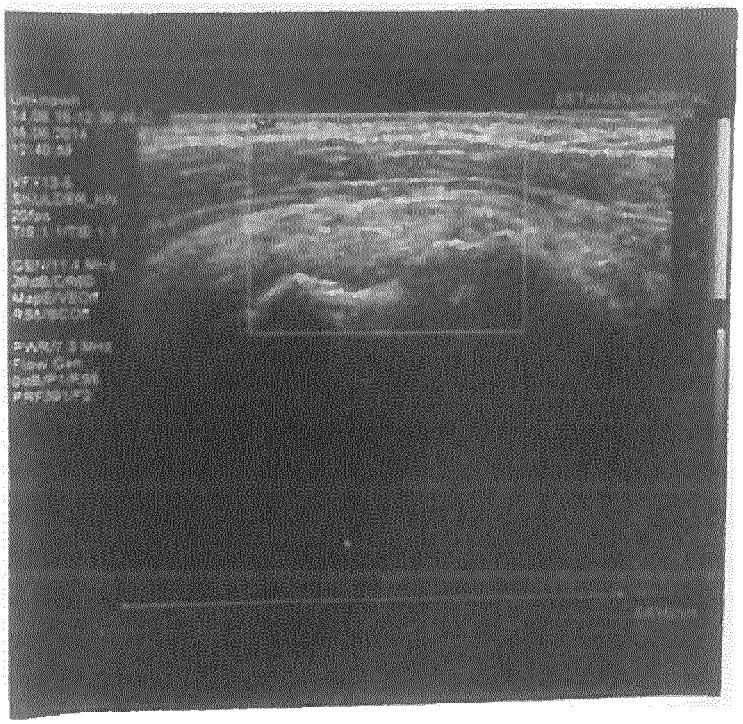
FIG. 2B shows no power Doppler in same shoulder.
Figure 2C:
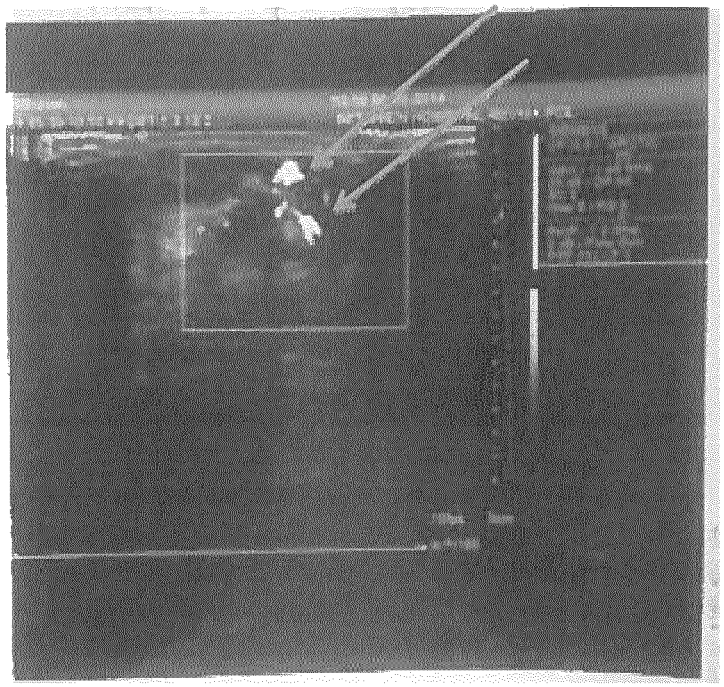
FIG. 2C shows white area highlighted by arrow, is power Doppler denoting inflammatory activity in right MCP 4 (finger joint) right side.
Figure 2D:
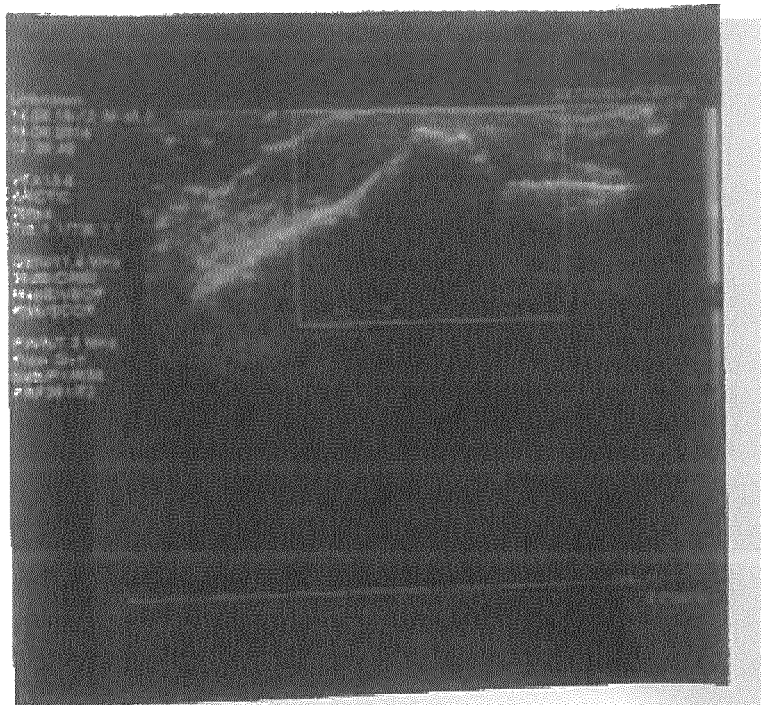
FIG. 2D shows no power Doppler in right MCP4 joint.
Figure 2E:
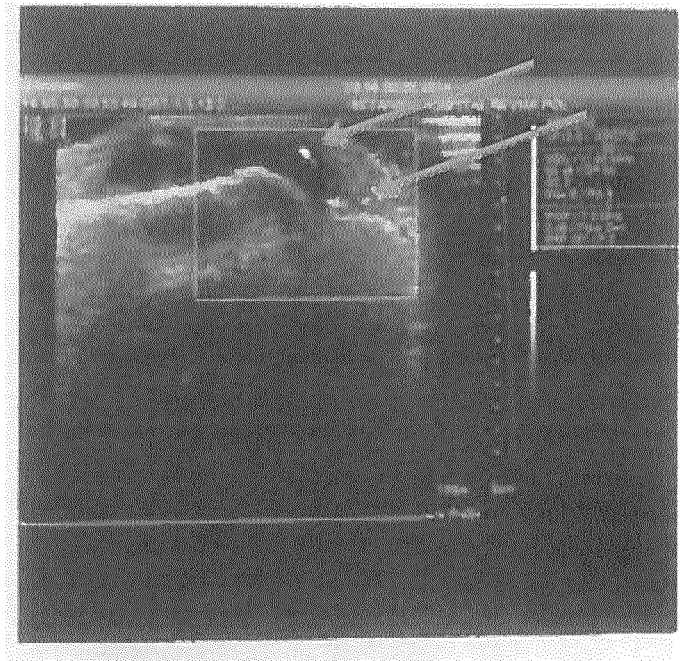
FIG. 2E shows white area highlighted by arrow, is power Doppler denoting inflammatory activity in right MCP 4 (finger joint) left side.
Figure 2F:
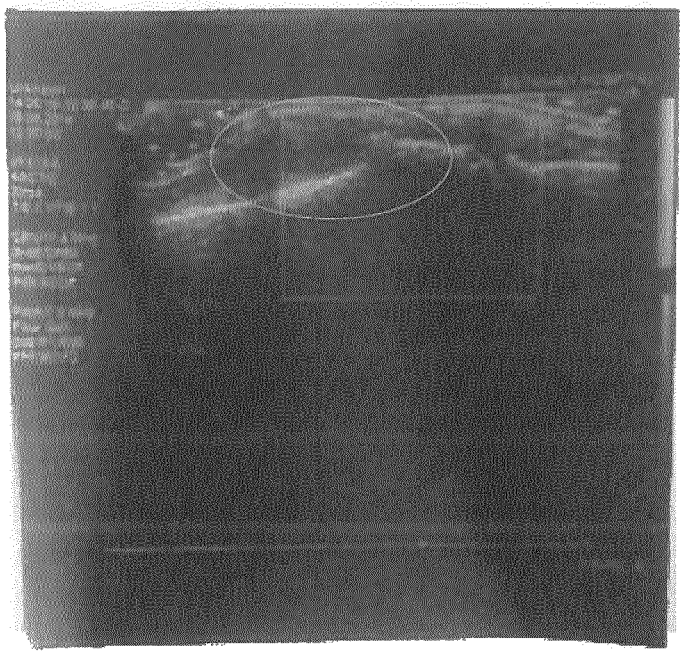
FIG. 2F shows no power Doppler in MCP 4 left side, and decreased joint fluid (oval).
Figure 5:
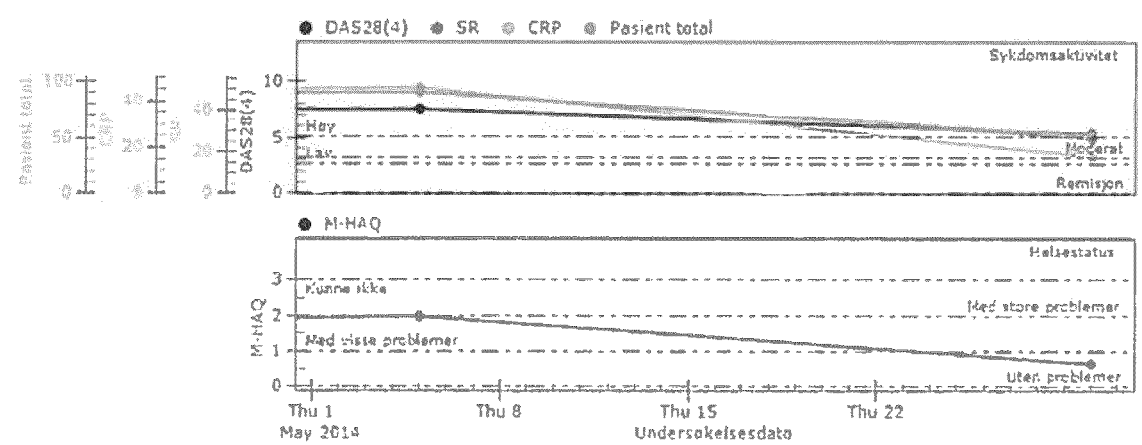
FIG. 5 shows disease activity variables of Patient 2 whilst being treated with degarelix.
Figure 6A:
FIG. 6 shows A and C, foot ulcers in a lupus patient prior to degarelix treatment and B and D, after degarelix treatment.
Figure 6B:
Figure 6C:
Figure 6D:

To facilitate an understanding of the present invention, a number of terms and phrases are defined below:

As used herein, the term "GnRH antagonist" refers to an agent or drug that decreases, blocks, inhibits, abrogates, or interferes with GnRH activity in vivo. For example, GnRH antagonists prevent or inhibit GnRH synthesis, and/or GnRH release, and/or GnRH function or activity. They may inhibit the action of GnRH by inhibiting binding of GnRH at its receptor, and may act at the GnRH receptor or at the GnRH molecule. The term "GnRH antagonist" thus includes compounds such as GnRH inhibitors, GnRH vaccinations such as GnRH-DT vaccinations consisting of the GnRH decapeptide linked to diphtheria toxoid, GnRH receptor antagonists, e.g. selective immune cell (e.g. T cell, B cell or macrophage cell) GnRH receptor antagonists, anti-GnRH antibodies, e.g. monoclonal antibodies against GnRH, circulating GnRH receptor fusion proteins, spiroindoline derivatives as gonadotropin-releasing hormone receptor antagonists, non-peptide oral GnRH antagonists, as well as agents which act to inhibit GnRH production and/or action by other mechanisms, for example by downregulating GnRH production due to negative feedback mechanisms, e.g. kisspeptin antagonists, estrogen compounds, testosterone compounds, luteinizing hormone (LH) compounds or follicle-stimulating hormone (FSH) compounds, hypothalamic hormones or neuropeptides. An oestrogen, testosterone, LH or FSH compound may be any compound or molecule or preparation which has oestrogen, testosterone, LH or FSH activity, including in particular oestrogen, testosterone, LH or FSH, or any preparation containing a said hormone, or a derivative of any said hormone. Examples of GnRH antagonists which may be used according to the invention are discussed further below. In one particular embodiment the GnRH antagonist acts to inhibit GnRH activity, e.g. by acting on or at the GnRH receptor or on GnRH itself (e.g. by binding to the receptor or GnRH). In some embodiments, a suitable GnRH antagonist prevents or inhibits GnRH receptor signaling. In some embodiments, a suitable 'GnRH antagonist' may be too large to cross the blood brain barrier. Such antagonist may take the form of a conjugate of a GnRH antagonist with a polymeric partner, e.g. a polymer such as a polypeptide (e.g. a protein such albumin), polysaccharide, or other polymer, such as polyethylene glycol (PEG) e.g. pegylated GnRH inhibitors, or GnRH inhibitors fused to proteins such as albumin. A polymer is defined broadly herein to include any compound having a multiplicity of repeating monomer units or residues and includes oligomers. A "multiplicity" may be 2 or more, e.g. 3, 4, 5, or 6 or more, but typically will be higher, e.g. 10, 12, 15, 18, 20, 25, 30, 35, 40, 45, 50, 60, 70, 80 or more. A polypeptide may accordingly include longer polypeptide sequences such as proteins as well as shorter peptides. Such conjugates of a GnRH antagonist with a polymer, and pharmaceutical compositions containing them, represent a novel aspect of this invention and are discussed further below.

Conjugates of a drug molecule/active agent with a polymer molecule are widely used and reported for drug delivery, as indeed is the use of polymers in formulation of drug delivery systems. The polymer may be water-soluble. The physical and chemical properties of the polymers typically used in polymer-drug conjugates are specially synthesized to flow through the kidneys and liver without getting filtered out, allowing the drugs to be used more effectively. Further, the polymer may be degraded e.g. through enzymes and acidity. Polymers may be synthesized to be sensitive to specific enzymes that are very apparent with diseased tissue. The drugs remain attached to the polymer and are not activated until the enzymes associated with the diseased tissue are present. This process significantly minimizes damage to healthy tissue. Any such polymer as is typically used in such drug delivery formulations or conjugates may be used to prepare a conjugate of a polymer with a GnRH antagonist according to the present invention. Examples include but are not limited to poly(ethylene glycol) (PEG), N-(2-hydroxypropyl)methacrylamide (HPMA), and poly(lactide-co-glycolide) (PLGA) copolymers.

The polymer of the conjugate, for example PEG or albumin, may act, or serve, to inhibit passage of the antagonist across the blood brain barrier. As used herein the term "inhibit", whether in this or any other context, includes reducing as well as preventing.

Many different classes of GnRH antagonist are known, including but not limited to peptide or polypeptide/protein-based antagonists and non-peptide small molecule organic compounds in a number of different chemical classes. A "small molecule" antagonist is defined herein as a non-peptide compound of size less than 2000 Da, more particularly less than 1500 or 1000 Da. Examples include relugolix, elagolix, spiroindoline derivatives and ASP1707.

A "peptide GnRH antagonist" is typically an analogue of the GnRH decapeptide, and may comprise one or more amino acid modifications and/or substitutions. A peptide GnRH antagonist may thus comprise a peptide chain, and may comprise one or more non-native or modified amino acids. Typically such an antagonist is 9 or 10 amino acids long, but may be shorter or longer. A number of such antagonists are known as described further below (e.g. degarelix, abarelix, ozarelix, cetrorelix, ganirelix).

The antagonists may be long acting or short-acting. A "long acting" antagonist may be defined as having a prolonged duration of action when administered to a subject in a single dose, e.g. at least 7, 12, 14, 15, 20, 30, 40, or 60 days, or at least 2, 4, 6, or 8 months. Exemplary long acting antagonists include the peptide antagonists degarelix, abarelix and ozarelix. By corollary, a "short acting" antagonist may have a duration of action of less than 7 days when administered to a subject in a single dose, more particularly less than, 6, 5, 4, 3, 2 days or 1 day. Exemplary short-acting GnRH antagonists include peptide antagonists such as cetrorelix and ganirelix, as well as non-peptide small molecule antagonists such as relugolix, elagolix, spiroindoline derivatives and ASP1707. A prolonged duration of action may also be achieved by formulating the antagonist as a sustained release or "depot" preparation or conjugate, e.g. with a protein such as albumin or salts and esters of acid derivatives, according to principles and procedures known in the art. As used herein, the term "subject" refers to any animal (e.g. a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but not limited to, vertebrates such as rodents, non-human primates, ovines, bovines, ruminants, lagomorphs, porcines, caprines, equines, canines, felines, ayes, etc.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

As used herein, the term "drug" is meant to include any molecule, molecular complex, prodrug, or substance administered to an organism for diagnostic or therapeutic purposes, including medical imaging, monitoring, contraceptive, cosmetic, nutraceutical, pharmaceutical and prophylactic applications. The term "drug" is further meant to include any such molecule, molecular complex or substance that is chemically modified and/or operatively attached to a biologic or biocompatible structure.

As used herein, the term "purified" or "to purify" or "compositional purity" refers to the removal of components (e.g. contaminants) from a sample or the level of components (e.g. contaminants) within a sample. For example, unreacted moieties, degradation products, excess reactants, or byproducts are removed from a sample following a synthesis reaction or preparative method.

The terms "test compound" and "candidate compound" refer to any chemical entity, pharmaceutical, drug, and the like that is a candidate for use to treat or prevent a disease, illness, sickness, or disorder of bodily function (e.g. cancer). Test compounds comprise both known and potential therapeutic compounds. A test compound can be determined to be therapeutic by screening using screening methods known in the art.

The terms "peripheral GnRH" or "inflammatory peripheral GnRH" mean that the subject has a GnRH level in the periphery of the body, that is outside the brain, which is elevated, or particularly elevated as compared with a reference subject does not have peripheral GnRH, or as compared to a normal reference peripheral GnRH (e.g. 0 to 160 pg/ml). Elevated peripheral levels of GnRH may be associated with inflammation or with an inflammatory condition (e.g. they may be indicative of an inflammatory condition, or may predispose to or cause or lead or contribute to an inflammatory condition), in particular with age-related inflammation, as part of the expected ageing process. Accordingly, increased levels of peripheral GnRH are proposed to be inflammatory (hence the use of the term "inflammatory peripheral GnRH"). A subject with peripheral GnRH may have a low level systemic inflammation (that is a generalised inflammation throughout the body), e.g. a chronic inflammation, but does not necessarily exhibit signs or symptoms of inflammatory disease. The subject may be healthy. More particularly, such a subject may have a level of peripheral GnRH which is 160 pg/ml or above, e.g. in the plasma or serum. Whilst not wishing to be bound by theory, the GnRH may be secreted by immune cells, specifically peripheral immune cells, for example T-cells. The GnRH may act upon the T-cells in a cytokine-like way, stimulating T-cell proliferation and maturation. GnRH may also act on B cells. A GnRH antagonist may act to combat peripheral inflammation by inhibiting the action of GnRH on immune cells, e.g. T and/or B cells, e.g. by inhibiting the effect of GnRH on GnRH receptors on such cells.

"Chronic inflammation" means an inflammation (e.g. an inflammatory condition) that is of persistent or prolonged duration in the body of a subject. Generally speaking this means an inflammatory response or condition of duration of 20, 25 or 30 days or more or 1 month or more, more particular of at least 2 or 3 months. Chronic inflammation leads to a progressive shift in the type of cells present at the site of inflammation. Chronic inflammation may occur as a result of persistent or prolonged injury or infection, prolonged exposure to toxic substances or by autoimmune responses or conditions. Chronic inflammation may be a factor in the development of a number of diseases or disorders, including particularly degenerative diseases, or diseases or conditions associated with loss of youthful function or ageing (e.g. as discussed above).

"Systemic inflammation" is inflammation which is not confined to a particular tissue or site or location in the body. The inflammation may be generalised throughout the body. Systemic inflammation typically involves the endothelium and other organ systems.

"Low-level inflammation" (which term is used herein as synonymous with "low-grade inflammation") is characterised by a 2- to threefold increase in the systemic concentrations of cytokines such as TNF-alpha IL-6 and CRP, e.g. as measured in the plasma or serum. The increase may be relative to, or as compared with, normal concentrations or reference concentrations, for example concentrations as determined in a particular reference cohort or population of subjects, e.g. young subjects (e.g. young adults) or healthy subjects, for example subjects who are not suffering from any disease or condition, including any inflammatory disease, or who do not have inflammation. The increase may also be relative to the level of concentration in a subject prior to development of the inflammation. Low-level inflammation may be observed in the absence of overt signs or symptoms of disease. Thus, low-level inflammation may be sub-clinical inflammation. Alternatively, a subject with low-level inflammation may not have a clinically diagnosed condition or disease, but may exhibit certain signs or symptoms of an inflammatory response or inflammatory condition. In other words, there may be signs or symptoms of the effect of inflammation in the body, but this may not yet have progressed to an overt or recognised disease. Low-level inflammation may be peripheral inflammation, that is more particularly inflammation associated with peripheral GnRH, as discussed above.

"Age-related inflammation" (or "age-associated-inflammation") is an inflammation, typically a chronic, particularly a chronic systemic inflammation which occurs with increasing age. Such inflammation may be observed above the age of 30, 35 or 40 but typically is seen in subjects aged 45, 50, 55 or 60 or more. In many cases this may be a low level inflammation.

"Cancer inflammation" is inflammation that occurs in the context of cancer and may alternatively be defined as "cancer-associated inflammation". Inflammation has been identified as a hallmark of cancer and may be necessary for tumorgenesis and maintenance of the cancer state. Cancer symptoms are associated with inflammation. Thus a subject with cancer may have or exhibit inflammation, which can be a low-level or peripheral inflammation as discussed above, and in particular a chronic or systemic inflammation as discussed above.

"Long-term" administration means that the GnRH antagonist is administered for a period of at least 12 weeks. This includes that the GnRH antagonist is administered such that it is effective over, or for, a period of at least 12 weeks and does not necessarily imply that the administration itself takes place for 12 weeks, for example if sustained release compositions or long acting antagonists are used. Thus, the subject is treated for a period of at least 12 weeks. In many cases, long-term administration is for at least 4, 5, 6, 7, 8, 9 months or more, or for at least 1, 2, 3, 5, 7 or 10 years, or more.

A "biologic" drug or agent, for example as typically used to treat an inflammatory disease such as rheumatoid arthritis, is any agent which is derived from, based on, or comprises a biological molecule. Typically, this may be an antibody, which term includes monoclonal and polyclonal antibodies, antibody fragments, and antibody derivatives such as e.g. chimeric humanised antibodies or single chain antibodies etc., or a another protein such as a receptor or receptor chain, domain or fragment.

DETAILED DESCRIPTION OF THE INVENTION

The present invention relates to screening, diagnosis, prognostic evaluation, and treatment or prevention of an inflammatory condition selected from age associated inflammation, chronic inflammation, and inflammatory diseases. In particular, the present invention relates to methods of treating inflammatory diseases (e.g., rheumatoid arthritis or spondyloarthritis) or patients with inflammatory peripheral GnRH with drugs that lower the effects of GnRH or GnRH inhibitors.

The stimulation of the hypothalamic-pituitary-gonadal (HPG) axis is related to systemic aging and lifespan. It has been shown that age-related hypothalamic changes occur independently of changes in gonadal hormones. GnRH pulse amplitude is increased and particularly erratic during the menopausal transition, when the risk for cardiovascular disease and osteoporosis is accelerated in females. Therefore, one may speculate that the pronounced rapid changes in GnRH and gonadotropin levels might be of particular importance in not only the pathogenesis of autoimmune diseases, where early menopause has been shown to be a risk factor, but also in the pathogenesis of cardiovascular disease and osteoporosis. This is also the time of the greatest and most erratic GnRH pulse amplitude as well as the greatest rate of unfavourable changes in lipid markers, and the greatest rate of bone mineral density loss in females.

GnRH is transported in a unique hypothalamic portal system and is rapidly degraded after reaching the pituitary. It has been suggested that the isolated hypophyseal portal system may not only have evolved solely as a means to deliver hypothalamic peptides to the pituitary, but also as a way to prevent their delivery to extra-pituitary targets. This is in accordance with a detrimental inflammatory GnRH.

There is a need for better treatments of inflammatory diseases, chronic inflammation, and therefore age-related inflammation.

The manuscript by Kass et al., Scandinavian Journal of Rheumatology, 2014; 43:22-27, describes a short term study of a GnRH antagonist, Cetrorelix (AGRA study). This is the first human study of GnRH antagonist treatment in an inflammatory disease. The study was conducted over a period of 5 days only and did not meet the primary end-point with regard to clinical response. However, some patients did show some response and the response was thought to be limited to patients with above normal levels of LH and FSH (Abstract to the 13$^{th}$ annual ACR meeting). The study did show a possible reduction of TNF-α. However, current TNF-α inhibiting therapy in rheumatoid arthritis is long term. The fact that TNF-α is acutely reduced by GnRH antagonists, as indicated in the AGRA study, does not show that GnRH antagonism is beneficial in rheumatoid arthritis or other inflammatory diseases using long term therapy. There are several examples in medicine that give positive immediate effects in disease but are unsuitable for long term use, either due to lack of efficacy, safety or both.

Prior to the present disclosure, a person skilled in the art would look for further data on the long term safety of GnRH antagonism in premenopausal females, postmenopausal females, and males. Degarelix, a depot GnRH antagonist, has only been tested in males over long term. Furthermore, Cetrorelix is actually contraindicated in postmenopausal females. In contrast, the present disclosure, in some embodiments, encompasses the long term use of GnRH antagonists in males, postmenopausal females, as well as premenopausal females. Examples of beneficial uses of medicines in rheumatoid arthritis over short term include high dose non-steroidal anti-inflammatory drugs or high dose intravenous steroids. These are treatments that must not be used over long term due to serious side effects. Side effects of GnRH antagonist therapy are believed to be osteoporosis and cardiovascular disease. As patients with rheumatoid arthritis are much more prone to osteoporosis and cardiovascular disease due to their systemic inflammation, a person skilled in the art would not attempt to treat these patients with long term GnRH antagonist therapy without further safety data, which the present disclosure provides. Furthermore, it is widely accepted that the reduction of oestrogen reduces bone density and contributes to cardiovascular disease. Therefore GnRH antagonists, which inhibit oestrogen, are expected to reduce bone density and contribute to cardiovascular disease.

Prior to the present disclosure, a person skilled in the art would have also looked for further data on the long term efficacy of GnRH antagonism in premenopausal females, postmenopausal females, and males. Maintenance doses for GnRH lowering drugs would be unknown, without further experimentation. The AGRA study was based upon a previous study (Kåss et al, The association of luteinizing hormone and follicle-stimulating hormone with cytokines and markers of disease activity in rheumatoid arthritis: a case control study, SJR 2010; 39: 109-17), which emphasized that the relative reduction of LH is important in improving disease activity. The study showed that low LH levels were not associated with low disease activity. That study also showed there was no association with absolute LH levels and disease activity, only relative changes of hormones. Therefore, one does not expect that stably low LH levels can show continued improvements in rheumatoid arthritis. There is no prior evidence to show that stably low levels of LH can be beneficial in rheumatoid arthritis. A relative reduction in LH can only be demonstrated at the initiation of therapy e.g. first 1-5 days. Indeed, that is why the AGRA trial was designed to give 5 days of therapy, for the greatest relative change in LH. Thereafter, with continued GnRH antagonist administration, levels will be stably low.

The AGRA study showed some short term anti-inflammatory effects in rheumatoid arthritis. However, the long term data with Degarelix, Cetrorelix and Ganirelix treatment in patients shows surprising unlikely improvements in severely ill patients. The mean disease activity score of the AGRA patients was 5.0, whereas the mean Degarelix disease activity score was 7.3 (scale 1.3-8.8, with higher numbers denoting greater disease activity); this supports a substantially greater disease activity in the Degarelix patients compared to patients in the AGRA study. Due to these baseline differences, the effects of Degarelix are surprising compared to the short term study.

Cetrorelix is used to treat hormone-sensitive cancers of the prostate and breast, and some benign gynaecological disorders. In addition, it is used in assisted reproduction to inhibit premature LH surges. The drug blocks the action of GnRH upon the pituitary, thus rapidly suppressing the production and action of LH and FSH. Both Cetrorelix and Ganirelix are administered as 0.25 mg daily s.c. injections. Degarelix is a depot monthly GnRH antagonist injection licensed for prostate cancer in males with a loading dose of 240 mg, and 80 mg monthly injections thereafter. The present disclosure provides different dosing schedules for patients with chronic inflammation.

Through studying long term GnRH antagonist treatment, we have also identified not only that stably low LH levels show continued improvements, but also any increase in LH, for example due to long intervals between Degarelix injections, can cause flares in RA patients. Therefore, in some embodiments, LH levels stay low throughout long term therapy.

The present disclosure provides the unexpected result that rheumatoid arthritis patients and other subjects with an inflammatory condition can be treated safely with a GnRH antagonist over the long term. Experiments described herein provide an example of a patient (patient 6 in Example 1) who did not improve in the short term study of 5 days, but improved surprisingly with long term treatment. The definition of long term treatment is treatment over 12 weeks according to FDA guidelines (Guidance for Industry Rheumatoid Arthritis: Developing Drug Products for Treatment May 2013). The disclosure also shows that long term therapy is safe and effective in postmenopausal females (previously contraindicated), premenopausal females, and males, without contributing to increased cardiovascular disease or osteoporosis as demonstrated by bone scans, laboratory variables and blood pressure, sometimes in combination with individual titration to baseline or higher levels of oestradiol or testosterone.

The disclosure further shows that stably low levels of LH contribute to continued improvements in rheumatoid arthritis.

Rheumatoid arthritis may develop, flare, or subside during hormonal changes in the HPG axis; for example, during pregnancy, postpartum, menopause, or aromatase inhibition therapy. These observations have prompted research into the effects of gonadal hormones of the HPG axis, such as oestrogen and testosterone in rheumatoid arthritis; but the results have been inconclusive.

Hypothalamic and pituitary hormones of the HPG axis control gonadal hormones. Gonadal hormones in both sexes are stimulated by pituitary LH and FSH. LH and FSH secretion are stimulated by the hypothalamic GnRH. GnRH, LH, and FSH have important physiological roles in both male and female reproduction. Therefore, these hormones may be involved in pathological processes in males as well as females.

Experiments conducted during the course of development of embodiments of the present invention demonstrated that GnRH-antagonism produced sustained long term anti-inflammatory effects in rheumatoid arthritis patients. Further experiments demonstrated that GnRH antagonists can be used to lower the amount of cytokines such as TNF-α, IL-1β, IL-10, and IL-2. Furthermore, the inventors show that GnRH antagonists reduce the levels of the acute phase protein CRP. Accordingly, embodiments of the present invention provide methods and uses of treating an autoimmune or inflammatory disease, comprising administering a GnRH antagonist to the subjects.

In one embodiment, the subjects are patients suffering rheumatoid arthritis. In some embodiments, subjects to be treated do not respond to methotrexate. In some embodiments, subjects to be treated do not respond to anti-TNF treatment. In some embodiments, the subjects to be treated do not respond to biologics as described above.

In some embodiments, subjects are women (e.g. post-menopausal women or women over age 40). In some embodiments, women are treated with a GnRH antagonist at a specific point in the menstrual cycle (e.g. midcyle when LH and FSH levels reach a high point). While not limited to a particular mechanism, it is contemplated that such treatment prevents premenstrual flare ups of RA symptoms. In some embodiments, subjects are men over age 40 (e.g. over age 50, 60, or 70).

In some embodiments, the patient population is defined as negative for CCP antibodies. In some embodiments, the patient population is defined as DMARD and/or TNF non responders.

Further experiments demonstrated that GnRH antagonists find use in the treatment and prevention of systemic lupus erythematosus, nephritis including lupus nephritis, ankylosing spondylitis, multiple sclerosis, scleroderma, psoriasis, inflammatory bowel disease, osteoporosis (e.g. by increasing bone mineral density), and cardiovascular disease (e.g. by decreasing HBA1c, decreasing blood pressure, or increasing HDL levels).

In some embodiments, the risk of cardiovascular disease is estimated in a variety of ways by a number of prognostic indicators. The Framingham Risk Score is based on data obtained from the Framingham Heart Study and is used to estimate the 10-year cardiovascular risk of an individual. The Framingham Risk Score is a calculated estimated risk for developing fatal or non-fatal cardiovascular event based on a composite score based on a pre-existing risk factors, including: age, gender, systolic blood pressure level (+/− treatment), HDL cholesterol level, and smoker status. A patient's risk score gives an indication of the likely benefits of prevention and also can be a useful metric to determine the effects of treatments.

The present invention is not limited to a particular GnRH antagonist or agent that alters the biological activity of GnRH. Examples include, but are not limited to, cetrorelix, elagolix, ganirelix, abarelix, degarelix, detirelix, iturelix, ozarelix, prazarelix, ramorelix, teverelix, elagolix, relogolix, or ASP1707. In some embodiments the present invention applies to any drug that prevents or inhibits GnRH receptor signaling. GnRH inhibitors, GnRH vaccines such as GnRH—DT the GnRH decapeptide linked to diphtheria toxoid, selective immune cell GnRH receptor antagonists, anti-GnRH antibodies, monoclonal antibodies against GnRH, circulating GnRH receptor fusion proteins, spiroindoline derivatives as gonadotropin-releasing hormone receptor antagonists, non-peptide oral GnRH antagonists, kisspeptin antagonists, estrogen compounds, testosterone compounds, LH compounds or FSH compounds, hypothalamic hormones or neuropeptides. In some embodiments, a suitable GnRH antagonist also prevents or inhibits GnRH receptor signaling. The antagonists may be used singly or in any combination.

As mentioned above, a wide variety of different GnRH antagonists are known and have been described in the literature, including both peptide and nonpeptide antagonists, the latter including antagonists in a large and varied range of different chemical classes. With regard to non-peptide small molecule GnRH antagonists reference may be made to the reviews by Heitman and Ijzerman, 2008, Med. Res. Rev., 28 (6), 975-1011 and Zhu and Chen, 2004, Expert Opin. Ther. Patents, 14 (2), 187-199, which reviews and the reference documents cited therein are all incorporated herein by reference.

Any of the GnRH antagonists known and described in the literature may be used. Known peptide antagonists include acetyl-β-[2-naphthyl]-D-Ala-D-p-chloro-Phe-β-[3-pyridyl]-D-Ala-Ser-Nε-[Nicotinoyl]-Lys-Nε-{Nicotinoyl}-D-Lys-Leu-Nε-[isopropyl]-Lys-Pro-D-Ala-NH$_2$ (Antide), acetyl D2Nal1, D4ClPhe2, D3Pal3, Arg5, Dglu6 (AA) (also known as NaIGlu), acetyl-D2NaI,D4ClPhe-D3Pal-Ser-Aph (Ac)-D-Aph(Ac)-Leu-Lys(lpr)-Pro-D-Ala-NH$_2$ (Abarelix, Praecis, Mass. US), Nal-Lys, Deslorelin, Histrelin, Nafarelin (Synarel, Searle Peapack, N.J.), Ganirelix (Orgalutron/Antagon) (Organon, West Orange, N.J.), Cetrorelix 1 ASTA Medica AG, Frankfurt, Germany), Cetrotide, Azaline B, Acryline (Ac-D2Nal-D4Cpa-D3Pal-Ser4-Aph(Ac)-D4Aph (Ac)-Leu-ILys-Pro-DAla-NH2), long-acting GmRH analogues incorporating p-ureido-phenylalanines at positions 5 and 6 (such as Degarelix (Ferring, Geneva, Switzerland)), FE200486, Ac-D2Nal-D4Cpa-D3Pal-Ser-4Aph(L-hydroorotyl)-D4Aph(carbamoyl)-Lei-ILys-Pro-DAla-NH2 (the acetate salt of which is FE200486), Ac-D2Nal-D4Cpa-D3Pal-Ser-4Aph(Atz)-D4Aph(Atz)-Leu-ILys-Pro-DAla-NH2 wherein Atz is 3'-amino-1H-1',2',4'-triazol-5'-yl,5, the antagonists described in U.S. Pat. Nos. 5,434,136, 6,156, 772, 6,156,767, 6,150,522, 6,150,522, 6,150,352, 6,147,088, 6,077,858, 6,077,847, 6,025,366, 6,017,944, 6,004,984, 5,998,432, and the GnRH antagonist described in *Poster Sessions*, Endo '98, p. 265 GnRH antagonists useful in the present invention may have a binding affinity that parallels the antagonistic properties and can be linear or cyclized pentapeptides to decappeptides. Of the linear peptide antagonists, peptides with Large substitutions in position 6, such as those found in Degarelix, or with large substitutions such as iodinated substitutions, lead to high binding affinity.

GnRH antagonists are also described in e.g. U.S. Pat. No. 5,470,947, WO 89/01944; U.S. Pat. No. 5,413,990; U.S. Pat. No. 5,300,492; U.S. Pat. No. 5,371,070, U.S. Pat. No. 5,296,468; U.S. Pat. No. 5,171,835; U.S. Pat. No. 5,003,011; U.S. Pat. No. 4,431,635; U.S. Pat. No. 4,992,421; U.S. Pat. No. 4,851,385; U.S. Pat. No. 4,801,5; and U.S. Pat. No. 4,689,396.

In another embodiment, the gonadotropin releasing hormone antagonist is a peptide, characterized by the structure: Ac-D-Nal-4-Cl-Phe-D-Pal-Ser-Tyr-D-Pal(N—O-Leu-Lys (iPr)-Pro-D-Ala-NH$_2$, or in another embodiment comprising a structure of Ac-D-Nal-4-Cl-D-Phe-D-Pal-Ser-Tyr-D-Pal (CH2-COO—)-Leu-Lys(iPr)-Pro-Ala-NH$_2$, or in another embodiment, Ac-Sar-4-Cl-D-Phe-D-Nal-Ser-Tyr-D-Pal (Bzl)-Leu-Lys(iPr)-Pro-Ala-NH$_2$ or a pharmaceutically acceptable salt thereof.

U.S. Pat. No. 5,516,887 describes antarelix ([Ac-D-2Nal$^1$, D-4ClPhe$^2$, D3 Pal$^3$, D-N$^\epsilon$-carbamoyl Lys$^6$, Ilys$^8$, D-Ala$^{10}$]-GnRH. U.S. Pat. No. 5,296,468 discloses the design and synthesis of a number of GnRH antagonists wherein the side chains of selected residues are reacted to create cyanoguanidino moieties, some of which subsequently spontaneously convert to a desired heterocycle, e.g. a 3-amino-1,2,4-triazole(atz). Such cyanoguanidino moieties are built upon the omega-amino group in an amino acid side chain, such as lysine, ornithine, 4-amino phenylalanine (4Aph) or an extended chain version thereof, such as 4-amino homophenylalanine (4Ahp). GnRH antagonists having such significantly modified or unnatural amino acids in the 5- and 6-positions exhibit good biological potency, and those build upon Aph are generally considered to be particularly potent.

Another example is Azaline B, i.e. [Ac-D-2Nal$^1$, D-4Cl-Phe$^2$, D-3 Pal$^3$, 4Aph(atz)$^5$, D-4Aph(atz)$^6$, ILys$^8$, D-Ala$^{10}$]-GnRH. U.S. Pat. No. 5,506,207 discloses GnRH antagonists with acylated, amino-substituted phenylalanine side chains of residues in the 5- and 6-positions; one such decapeptide is Acyline, [Ac-D-2Nal$^1$, D-4ClPen$^2$, D-3 Pal$^3$, 4Aph(Ac)$^5$, D-4Aph(Ac)$^6$, ILys$^8$, D-Ala$^{10}$]-GnRH.

Peptide antagonists generally may be subject to degradation in the GI tract and so tend to be administered parenterally, typically by injection, e.g. subcutaneously or intramuscularly.

As regards small molecule-peptide GnRH antagonists, at least 14 different chemical classes of compounds have been reported. Many such antagonists have the advantage that they may be administered orally. The chemical classes include thieno[2,3-d]pyridin-4-one derivatives, quinolin-2-one derivatives, indole derivatives, pyrrolo [1,2-a]pyrimid-7-one derivatives, imidazolo[1,1-a]pyramidin-5-one derivatives, thieno[2,3-d]pyrimidin-2,4-dione derivatives, furamide derivatives, pyrimidin-2,4-dione derivatives, benzimidazole derivatives, 1,3,5-triazine-2,4,6-trione derivatives, thiazolino[3,2-c]pyramidin-5,7-diones and oxazole derivatives thereof, tetrahydropyrido[4,3,d]pyrimidin-2,4-dione derivatives, tetrahydropyrrolo[3,2-c]pyridines, thieno[2,3-b]pyrolle derivatives, 3-pyrazinone, pyrid-2-one and pyrid-4-one derivatives, various other pyrazole and pyrrole derivatives, oxazole- and thiazole-4-carbamide compounds, tetrahydroisoquinoline derivatives. 1,3-dihydrobenzimidazole derivatives, imidazo[1,2-a]pyridines, bicyclic pyrrolidines, qujnolines, imidazo[4,5-c]pyridines, benzimidazoles, benzoxazoles, benzothiazoles, quinazoline-2,4-diones, tricyclic pyrrolidines, 1,2,3,4-tetrahydro carbazoles. More recently, certain spiroindoline derivatives have been found to have GnRH antagonists activity. GnRH receptor antagonists have thus been described with a wide range of diverse chemical structures. Spiroindoline GnRH antagonists are described in WO2014166958 (Bayer), which is incorporated herein by reference. Representative examples of such spiroindoline compounds include compounds of the following Formula 1

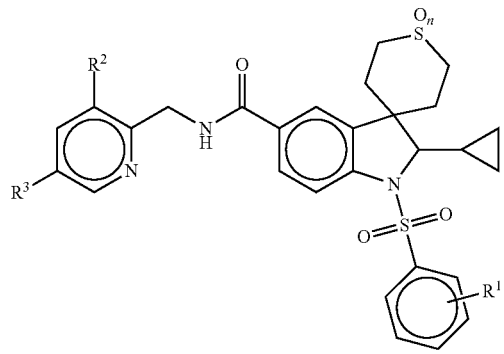

n = 0, 1, 2

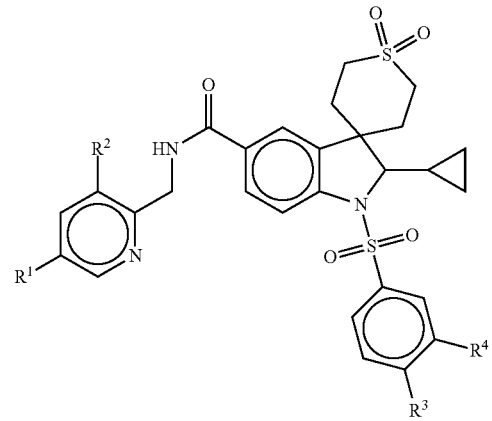

2 R$^1$ = Cl, R$^2$ = CF$_3$, R$^3$ = F, R$^4$ = H
3 R$^1$ = CF$_3$, R$^2$ = F, R$^3$ = H, R$^4$ = CN
4 R$^1$ = CF$_3$, R$^2$ = Cl, R$^3$ = H, R$^4$ = OCF$_3$
5 R$^1$ = CF$_3$, R$^2$ = Cl, R$^3$ = Cl, R$^4$ = H

The compounds may be prepared as racemic mixtures and resolved into two enantiomers by using chiral column chromatography methods.

Reference may also be made to the following exemplary patent applications describing the various different GnRH antagonists, which also incorporated herein by reference: WO 95/28405, WO 97/14697, WO 97/41126, WO/000 0493, WO96/24597, WO00/56739, WO99/33831, U.S. Pat. No. 6,413,972 (Takeda); WO99/21557, WO99/41252, WO00069433, WO99/51231, WO99/51595, WO00/53602, WO97/44037, WO01/0228 (Merck and Co); WO00/69859, WO015519, WO03/011293, WO 03/011841, WO03011870 (Neurocrine Bioscience Inc); WO99/44987 (Alanex Corp.); WO03/06879 (Agouron Pharm. Inc); WO02/092565, WO 02/066478, WO02/066477 (AstraZeneca); WO02/11732 (Glaxo Group Ltd); WO02/066437 (Schering); WO02/48112 (OrthoMcNeil Pharm. Inc); WO03/053939 (SCRAS); WO02/02533 (Yamanouchi Pharm. Co).

Many GnRH antagonists may be obtained commercially. Degarelix is marketed under the name Firmagon by Ferring. Ganirelix is described in U.S. Pat. No. 5,767,082, and U.S. Pat. No. 6,653,286 and is available from Merck/MSD. Cetrorelix is available from Merck Serono. Relugolix is available from Takeda. Elagolix is available from Abbvie/Neurocrine Biosciences Inc. ASP1707, a benzimidazoylidene propane-1,3-dione derivative and other propane-1,3-dione derivatives are described in WO 2005/118556, U.S. Pat. No. 8,076,367 and U.S. Pat. No. 7,569,688.

ASP1707 is available from Astellas. Spiroindoline derivatives are available from Bayer. A GnRH-DT vaccine is available from GSK. Various pyrazole and pyrrole compounds are available from AstraZeneca.

In some embodiments, a suitable 'GnRH antagonist' may be too large to cross the blood brain barrier (BBB). As described above, in one embodiment such large antagonists may be provided by coupling or conjugating a GnRH receptor antagonist to a polymer, including particularly a polymer selected from a polypeptide, a polysaccharide, a polyethylene glycol or HPMA or a PLGA copolymer. The polypeptide may typically be a protein such as albumin, or the Fc part of an antibody. The polysaccharide may for example be a dextran etc. Thus such a non-BBB crossing GnRH antagonist may include pegylated GnRH inhibitors, or GnRH inhibitors fused to proteins such as albumin. These conjugates may be administered via several routes, including but not limited to subcutaneous and oral routes.

Accordingly, any of the GnRH antagonists described above may be coupled to a polymer, including particularly peptide antagonists such as degoralix, cetrorelix or ganirelix, or small molecule non-peptide antagonists such as elagolix, relugolix, ASP1707, or a spiroindoline derivative.

Such conjugates represent a novel aspect of the present invention. Accordingly, in a further aspect the present invention provides a conjugate comprising a GnRH antagonist linked to a polymer, more particularly a polymer which serves (more particularly specifically serves) to inhibit passage of the GnRH antagonists across the BBB. Such a conjugate may be used for the treatment or prevention of any inflammatory condition, as defined and discussed above.

In a further aspect, the invention accordingly provides such a conjugate for use in therapy.

In a still further aspect, the invention provides a pharmaceutical composition containing a conjugate of the invention as herein defined, together with at least one pharmaceutically acceptable carrier or excipient.

Such GnRH conjugates may readily be prepared using well known procedures and reagents, as described in the art. Thus, a variety of different methods and reagents for linking peptides or non-peptide small organic molecules to polymers such as proteins or other polypeptides, polysaccharides or polyethylene glycol are available and would be known to the person skilled in this art. The GnRH antagonists may be linked directly or indirectly, e.g. via a spacer or linker group, to the polymer.

The conjugates of the invention have particular utility in long term treatment of an inflammatory condition, but are not limited to such use. In a particular embodiment they have utility in the treatment of chronic inflammation, age-related inflammation or inflammatory peripheral GnRH. In this regard, such conjugates are advantageous in that by not being able to cross the BBB, they do not act centrally (in other words they are inhibited from acting at central GnRH receptors, that is GnRH receptors on the pituitary). In this way undesirable side-effects may be avoided, and in particular side-effects comprising or involving inhibition of sex hormone (e.g. oestrogen or testosterone) production and/or action.

It would be highly advantageous if one could only access peripheral GnRH receptors without disturbing central GnRH receptors. For long term treatment, e.g. of several years, in e.g. chronic inflammation, this avoids side effects of decreasing FSH, LH, oestrogen, and testosterone. Therefore, one avoids disrupting menstrual cyclicity in premenopausal women, in order to maintain fertility. Prior to the present disclosure one would have anticipated that GnRH antagonists should only work centrally on pituitary gonadotropes. The present disclosure describes the treatment of inflammatory peripheral GnRH, that contributes to chronic inflammation and age associated inflammation. This feature of GnRH inhibition is possible through drugs that lower the peripheral effects of GnRH without crossing the BBB. Such compounds would have to be larger than the currently available GnRH antagonists which do cross the BBB. Examples include, but are not limited to, a larger GnRH antagonist such as a GnRH antagonist attached to albumin, or a pergylated GnRH antagonist, which are producible by persons skilled in the art. The same may be applied to other hormones, peptides, or substances that are involved in the regulation of GnRH including, but not limited to, kisspeptin. Various modifications and variations of the described method and system of the invention will be apparent to those skilled in the art without departing from the scope and spirit of the invention.

The present invention further provides the use of a GnRH antagonist in the treatment of an autoimmune disease in a subject.

The present invention is not limited to the treatment of a particular autoimmune or inflammatory disease. In some embodiments, the disease is rheumatoid arthritis. In some embodiments, inflammatory diseases include but are not limited to arthritis, inflammatory bowel disease, psoriatic arthritis, osteoarthritis, degenerative arthritis, polymyalgia rheumatic, ankylosing spondylitis, reactive arthritis, gout, pseudogout, inflammatory joint disease, systemic lupus erythematosus, polymyositis, and fibromyalgia. Additional types of arthritis include achilles tendinitis, achondroplasia, acromegalic arthropathy, adhesive capsulitis, adult onset Still's disease, anserine bursitis, avascular necrosis, Behcet's syndrome, bicipital tendinitis, Blount's disease, brucellar spondylitis, bursitis, calcaneal bursitis, calcium pyrophosphate dihydrate deposition disease (CPPD), crystal deposition disease, Caplan's syndrome, carpal tunnel syndrome, chondrocalcinosis, chondromalacia patellae, chronic synovitis, chronic recurrent multifocal osteomyelitis, Churg-Strauss syndrome, Cogan's syndrome, corticosteroid-induced osteoporosis, costosternal syndrome, CREST syndrome, cryoglobulinemia, degenerative joint disease, dermatomyositis, diabetic finger sclerosis, diffuse idiopathic skeletal hyperostosis (DISH), discitis, discoid lupus erythematosus, drug-induced lupus, Duchenne's muscular dystrophy, Dupuytren's contracture, Ehlers-Danlos syndrome, enteropathic arthritis, epicondylitis, erosive inflammatory osteoarthritis, exercise-induced compartment syndrome, Fabry's disease, familial Mediterranean fever, Farber's lipogranulomatosis, Felty's syndrome, Fifth's disease, flat feet, foreign body synovitis, Freiberg's disease, fungal arthritis, Gaucher's disease, giant cell arteritis, gonococcal arthritis, Goodpasture's syndrome, granulomatous arteritis, hemarthrosis, hemochromatosis, Henoch-Schonlein purpura, Hepatitis B surface antigen disease, hip dysplasia, Hurler syndrome, hypermobility syndrome, hypersensitivity vasculitis, hypertrophic osteoarthropathy, immune complex disease, impingement syndrome, Jaccoud's arthropathy, juvenile ankylosing spondylitis, juvenile dermatomyositis, juvenile rheumatoid arthritis, Kawasaki disease, Kienbock's disease, Legg-Calve-Perthes disease, Lesch-Nyhan syndrome, linear scleroderma, lipoid dermatoarthritis, Lofgren's syndrome, Lyme disease, malignant synovioma, Marfan's syndrome, medial plica syndrome, metastatic carcinomatous arthritis, mixed connective tissue disease (MCTD), mixed cryoglobulinemia, mucopolysaccharidosis, multicentric reticulohistiocytosis, multiple epiphyseal dysplasia, mycoplasmal arthritis, myofascial pain syndrome, neonatal lupus, neuropathic arthropathy, nodular panniculitis, ochronosis, olecranon bursitis, Osgood-Schlatter's disease, osteoarthritis, osteochondromatosis, osteogenesis imperfecta, osteomalacia, osteomyelitis, osteonecrosis, osteoporosis, overlap syndrome, pachydermoperiostosis Paget's disease of bone, palindromic rheumatism, patello femoral pain syndrome, Pellegrini-Stieda syndrome, pigmented villonodular synovitis, piriformis syndrome, plantar fasciitis, polyarteritis nodos, Polymyalgia rheumatic, polymyositis, popliteal cysts, posterior tibial tendinitis, Pott's disease, prepatellar bursitis, prosthetic joint infection, pseudoxanthoma elasticum, psoriatic arthritis, Raynaud's phenomenon, reactive arthritis/Reiter's syndrome, reflex sympathetic dystrophy syndrome, relapsing polychondritis, retrocalcaneal bursitis, rheumatic fever, rheumatoid vasculitis, rotator cuff tendinitis, sacroiliitis, *salmonella* osteomyelitis, sarcoidosis, saturnine gout, Scheuermann's osteochondritis, scleroderma, septic arthritis, seronegative arthritis, *shigella* arthritis, shoulder-hand syndrome, sickle cell arthropathy, Sjogren's syndrome, slipped capital femoral epiphysis, spinal stenosis, spondylolysis, *staphylococcus* arthritis, Stickler syndrome, subacute cutaneous lupus, Sweet's syndrome, Sydenham's chorea, syphilitic arthritis, systemic lupus erythematosus (SLE), Takayasu's arteritis, tarsal tunnel syndrome, tennis elbow, Tietse's syndrome, transient osteoporosis, traumatic arthritis, trochanteric bursitis, tuberculosis arthritis, arthritis of Ulcerative colitis, undifferentiated connective tissue syndrome (UCTS), urticarial vasculitis, viral arthritis, Wegener's granulomatosis, Whipple's disease, Wilson's disease, and yersinial arthritis.

In some embodiments, the GnRH or gonadotropin antagonist is administered in combination with an additional treatment i.e. additional active agent (e.g. treatments or agents known to be useful or effective in the treatment of autoimmune or inflammatory disease such as rheumatoid arthritis). Such an additional active agent may accordingly be a disease-modifying drug and in particular a disease-modifying drug for use in treating or preventing inflammation or an inflammatory condition as defined herein. Examples of such agents include, but are not limited to, disease-modifying antirheumatic drugs (e.g. leflunomide, methotrexate, sulfasalazine, hydroxychloroquine), disease-modifying agents for use in treating multiple sclerosis (e.g. Famprydine), biologic agents (e.g. rituximab, infliximab, etanercept, adalimumab, golimumab, tofacitinib, anakinra, abatacept), nonsteroidal anti-inflammatory drugs (e.g. ibuprofen, celecoxib, ketoprofen, naproxen, piroxicam, diclofenac), analgesics (e.g. acetaminophen, tramadol), steroids and glucocorticoids (e.g. prednisone, methylprednisone), and therapies for osteoporosis such as Fosamax or Zolendronic acid.

In a further aspect the invention also provides a GnRH antagonist for use in the treatment or prevention of an inflammatory condition in a subject, selected from an inflammatory disease, chronic inflammation, age-related information or inflammatory peripheral GnRH, wherein said GnRH antagonist is for co-administration to said subject together with a further active agent, and in particular wherein said further active agent is a disease-modifying drug, or a sex hormone or an agent which regulates sex hormone production and/or activity (e.g. an agent useful in sex hormone substitution therapy).

A sex hormone may be oestrogen or testosterone or an oestrogen or testosterone derivative. Such oestrogen or testosterone derivatives are widely described in the art and available commercially. Likewise agents useful in sex hormone substitution therapy are also well known in the art and widely available, and include for example LH or FSH or LH or FSH derivatives or analogues.

In an embodiment the further active agent may be useful in, or effective for, the treatment of an inflammatory condition, e.g. an inflammatory disease including an inflammatory disease as defined herein. The further active agent may be as described above. In a particular embodiment of this aspect of the invention, the GnRH antagonist may be for long-term administration.

This aspect of the invention also provides kits or combined/combination products containing or comprising a GnRH antagonist and an additional active agent. In particular, such kits or combined/combination products are for use in treating or preventing an inflammatory condition as defined herein.

The GnRH antagonist and additional active agent may be formulated for administration together, e.g. in a single pharmaceutical composition, or they may be formulated for separate, e.g. sequential or simultaneous, or substantially simultaneous, administration. Thus, the kit or combined/combination product may comprise separate containers, each containing a GnRH antagonist and a further active agent.

The GnRH antagonist and the additional active agent may be administered by the same route or by different routes. Thus for example in one embodiment the GnRH antagonist may be administered parenterally, e.g. by injection (e.g. subcutaneous or intramuscular injection) and the additional active agent may be administered orally. In other embodiments both the components may be administered orally, or both may be administered parenterally e.g. by injection.

In a particular aspect, the invention provides a product (e.g. a kit) comprising a GnRH antagonist and an additional active agent as a combined preparation for simultaneous, separate or sequential use in the treatment or prevention of an inflammatory condition in a subject, selected from an inflammatory disease, chronic inflammation, age-related inflammation or inflammatory peripheral GnRH, wherein said additional agent is useful in the treatment of said inflammatory condition.

In a preferred embodiment said GnRH antagonist and additional active agent are for long-term administration to said subject for a period of at least 12 weeks.

Certain Examples included below demonstrate that the GnRH antagonists when administered with an additional active agent may exhibit synergy. There may be an additional, e.g. greater than cumulative, effect when the additional active agent is co-administered with a GnRH antagonist. In other embodiments, the clinical benefit experienced by the subject may be improved or augmented in any way, when the GnRH antagonist is co-administered with the additional active agent. Synergistic combinations of a GnRH antagonist and an additional active agent represent one preferred embodiment of the invention.

When the condition being treated is arthritis, the additional agent can be an agent effective in treating arthritis (e.g. TNF-α inhibitors such as anti-TNF a monoclonal antibodies (such as REMICADE®, CDP-870 and HUMIRA™ (adalimumab) and TNF receptor-immuno-globulin fusion molecules (such as ENBREL®) (entanercept), IL-1 inhibitors, receptor antagonists or soluble IL-1R α (e.g. KINERET™ or ICE inhibitors), nonsteroidal anti-inflammatory agents (NSAIDS), piroxicam, diclofenac, naproxen, flurbiprofen, fenoprofen, ketoprofen ibuprofen, fenamates, mefenamic acid, indomethacin, sulindac, apazone, pyrazolones, phenylbutazone, aspirin, COX-2 inhibitors (such as CELEBREX® (celecoxib), VIOXX® (rofecoxib), BEXTRA® (valdecoxib) and etoricoxib, (preferably MMP-13 selective inhibitors), NEUROTIN®, pregabalin, sulfasalazine, low dose methotrexate, leflunomide, hydroxychloroquine, d-penicillamine, auranofin, parenteral or oral gold), rituximab, roactemera, or orencia. The additional agents to be co-administered can be any of the well-known agents in the art, including, but not limited to, those that are currently in clinical use.

In some embodiments the GnRH antagonist is administered in combination with hormone substitution therapy (e.g. testosterone, such as Testogel 50 mg every 1-5 days, oestrogen, such as Activelle 1 mg/0.5 mg every 1-5 days, luteinizing hormone, such as 75IE lutropin alfa daily, or every 2-5 days, or follicle stimulating hormone, such as 75-150IE follitropin alfa daily, or every 2-5 days.

In some embodiments, the patients receive oestrogen or testosterone supplement daily or every 2-6 days or weekly, in addition to GnRH antagonist.

In some embodiments, the physician titrates the dose of oestrogen or testosterone to the patient's baseline or higher levels.

Accordingly, in a representative embodiment, where the additional active agent is a sex hormone or an agent effective for hormone substitution therapy, the dose of the sex hormone or other agent is titrated to achieve a desired or selected oestrogen or testosterone level in the subject, for example a level which is substantially equal to or higher than a baseline level, or in some cases lower than a baseline level. Such a baseline level may be the level of the subject prior to administration of the GnRH antagonist, or it may be a reference baseline level, for example a level of oestrogen or testosterone which is a normal level or which is a typical level for that subject (e.g. an age- and/or sex-matched subject or a healthy subject of the appropriate gender). An appropriate or desired level may be selected according to need or circumstance, for example based on the age, sex and/or clinical condition of the patient. Thus, for example, as a patient ages a lower level may be appropriate, particularly over a long course of treatment over many years. Thus, the desired or appropriate level may change.

In some embodiments, the GnRH antagonist is continually administered, or given as a vaccination with booster doses, or administered in one or more repeated doses (e.g. up to 6 times daily, e.g. 2, 3 or 4 to 6 times daily, daily, weekly, monthly, or other interval) for a period of time (e.g. at least three months, at least 6 months, at least 9 month, at least 12 months or longer). (Although, as indicated above, in aspects of the invention which are not limited to administration for at least 12 weeks, shorter administration periods may be possible, at least one week, at least two weeks, at least one month, or at least two months). As noted above, in other embodiments the GnRH antagonist may be administered for at least 1, 2, 3, 5, 6, 7, 8, 9, 10 or 20 years or longer. In some embodiments, short acting or long acting formulations are utilized.

The GnRH antagonist may be administered by any convenient or desired route, including both parenterally or enterally. In some embodiments, the GnRH antagonist is administered subcutaneously, intramuscularly, intravenously, dermally, orally, infusion pump, or intraarticularly. Administration may be for example by injection or infusion or by other means of local or systemic delivery. In some embodiments, GnRH antagonists are administered up to 6 times daily or weekly or every 2-4 week intervals, or monthly intervals or every 2-6 month intervals, or yearly, 0.1 mg to 3000 mg, e.g. 10 mg to 1000 mg. In some embodiments with an initial loading dose between 20 mg to 1000 mg.

In some embodiments, a long acting GnRH antagonist, e.g Degarelix, Ozarelix or Abarelix is administered weekly, or every 2-4 week intervals, or monthly intervals or every 2-6 month intervals, or yearly, 10 mg to 1000 mg. In some embodiments, with an initial loading dose of the long acting GnRH antagonist between 20 mg to 1000 mg.

In a particular embodiment a long-acting antagonist (which may be a long-acting peptide antagonist, e.g. degarelix, or a sustained release preparation of a GnRH antagonist) is administered at an initial loading dose of 20 to 100 mg, followed by a maintenance dose of 40-1000 mg every 10-14 days, e.g. every 2 weeks. For example, the maintenance dose may be 60-1000, 80-1000, 100-1000, 60-800, 60-500, 80-800, 80-500, 100-800, 100-500, 80-400, 80-320, 60-400, 60-320, 60-160, 80-160, 60-150, 80-150 mg or any range between any of the above-mentioned integers.

In another embodiment, maintenance dose may be administered every 5 to 10 days, e.g. every 7 days or every week. The maintenance dose may be in the range as indicated above or may be 30-1000, 30-800, 30-500, 30-400, 30-320, 30-320, 30-200, 30-150 mg, or it may be 40 or 50 mg to any one of 1000, 800, 500, 400, 320, 300, 250, 200, 180, 160 or 150 mg.

In some embodiments, short acting GnRH antagonists, e.g. peptide antagonists such as Cetrorelix or Ganirelix are administered up to 6 times daily (e.g. 2, 3 or 4 to 6 times daily) or daily or 2-6 times weekly or weekly or every 2-4 weeks, e.g. at a dose of 0.1 mg to 30 mg. In particular, the antagonist may be administered at a dose of any one of 0.1, 0.5, 0.75, 1, 2, 3, 4, 5, 6, 7, 8, 9 or 10 mg to any one of 20, 30, 40, 50, 60, 70, 80, 90 or 100 mg.

In some embodiments, an oral GnRH antagonist such as nonpeptide oral GnRH antagonists, spiroindoline derivatives as GnRH antagonists, Relugolix, Elagolix, or ASP1707 is administered up to 6 times daily (e.g. 2, 3 or 4 to 6 times daily), or daily, or 2-6 times weekly or weekly, e.g at a dose of 0.1 mg to 3 g.

For example Elagolix may be administered at a dose of 10 to 2000 mg/day, e.g. 200 to 800, 200 to 600, 200 to 500, 300 to 800, 300 to 600, 300 to 500, 550 to 750, 750 to 1000 mg/day, e.g 400 or 500 mg/day.

Relugolix may be administered at a dose of 10 to 1000 mg/day, e.g. a 20-100, 50-200, 100-500, 500-1000 mg/day, e.g. 400 mg/day.

ASP1707 may be administered at a dose of 0.5-50 mg/day, e.g. 1-20, 1-15, 1-10, 2-10, 3-10 e.g. 10 mg/day.

A spiroindoline derivative may be administered at a dose of 0.1 to 1000 mg/day, e.g. 0.1 to 10, 0.5 to 150, 150 to 500, 550 to 750 e.g. 200 mg/day.

In general, we propose that a GnRH antagonist may be administered at a higher dose than is presently proposed for uses of GnRH antagonists in the art, particularly where such antagonists are used for treating hormone-related problems, e.g. prostate cancer, fibroids or endometriosis, or for fertility treatment. For example such doses or concentrations may be 3 or 4 times higher than typical, conventional or normal doses or concentrations, e.g. doses or concentrations for such treatments.

As noted above, the GnRH antagonists are proposed according to the invention described above for administration on a long-term basis, that is for at least 12 weeks. However in a separate and alternative aspect also included according to the invention is the administration of a GnRH antagonist at the doses indicated above, but without limitation to an administration period of at least 12 weeks.

In some embodiments, 'healthy' people or 'unhealthy' people are identified with increased levels of peripheral GnRH using ELISA GnRH detection kits, PET scans for the detection of GnRH activity, tissue staining, or otherwise i.e. screened, diagnosed, or prognostically evaluated for age associated inflammation, or chronic inflammation or inflammatory disease, with the aim of possible treatment initiation. Some of these people may fulfill criteria for diagnosis of an inflammatory disease or show signs or symptoms of chronic inflammation and some may not. These people can be, but are not limited to, otherwise healthy people with normal blood pressure, normal cholesterol and normal high sensitivity CRP, or other. These people may also be people who have cardiovascular disease or osteoporosis. If the presence of peripheral GnRH has been identified, for example between 30 pg/mL to 1500 pg/mL, or between 20 pg/ml to 5000 mg/ml, or through another method, these people may be offered a drug to lower the effects of peripheral GnRH. In some embodiments, the detrimental effects of peripherally detectable GnRH are expected to decrease with treatment which decreases the effects of GnRH over time. It may be necessary to individually titrate levels of altered downstream hormones, for example oestrogen or testosterone.

In some embodiments, the detection of peripheral GnRH will be positively associated with the amount of systemic inflammation or the rate of increase of systemic inflammation. This is a method for the prognostic evaluation for disease(s) caused by inflammation.

GnRH is thought to be only detectable in the brain. GnRH is rapidly degraded after reaching the pituitary. It has been suggested that the isolated hypophyseal portal system may not only have evolved solely as a means to deliver hypothalamic peptides such as GnRH to the pituitary, but also as a way to prevent their delivery to extra-pituitary targets resulting in unfavorable outcomes, such as systemic inflammation or age associated inflammation. Through the detection of GnRH activity outside the brain, people can be screened, diagnosed, evaluated, and treated for age associated inflammation, chronic inflammation or inflammatory diseases. Thus, the present invention in a further aspect provides a GnRH antagonist for use in the treatment or prevention of peripheral inflammation, or systemic inflammation, or chronic low level inflammation (particularly chronic systemic low level inflammation), including age-related inflammation (e.g. low level age-related inflammation).

In one embodiment, the invention provides a GnRH antagonist for use in the treatment or prevention of inflammatory peripheral GnRH. More particularly, the subject has a peripheral GnRH level of 160 pg/ml or more, e.g. as measured in plasma or serum. In other embodiments, the subject may have a peripheral GnRH level of at least 120% of the concentration of healthy control subject(s), 100, 200, 320, 350, 370, 380, 400, 420, 450, 470, 480 or 500 pg/ml or more.

In such aspects and embodiments the GnRH antagonist is preferably administered long term for at least 12 weeks.

Peripheral GnRH may be measured or determined in a sample of any body tissue or fluid taken from the subject at or from a site or location outside of the brain (i.e. from the periphery of the body). Conveniently, the GnRH may be determined in a blood or a blood-derived sample, particularly serum or plasma, but this can be in any other blood-derived preparation. Other representative samples include vascular tissue and synovial fluid.

The GnRH may be determined or measured by any method or technique known in the art. Conveniently an immunoassay may be used. More particularly, an immunoassay may be performed using an antibody (or antibody fragment or antibody derivative etc.) which binds specifically to GnRH, and the binding of the antibody to GnRH is detected or determined, e.g. an ELISA, and kits for performing such assays are commercially available. Alternatively, GnRH may be detected with histochemical and/or histological techniques e.g. immunohistochemical techniques.

Alternatively, peripheral GnRH may be determined by assays or methods carried out in in vivo on the body, e.g. by imaging techniques. Thus for example a PET scan may be performed for GnRH activity, e.g. using a GnRH antagonist radiolabelled with positron emitting nuclides for visualising GnRH receptors.

In particular embodiments of these aspects, the subject may be a subject who does not have or exhibit any signs or symptoms of an inflammatory disease. Accordingly, in particular embodiments the subject may have a sub-clinical inflammatory condition, or may be without overt symptoms of disease, or overt clinical symptoms of disease, or may be healthy. Thus, as noted above, the subject may have normal blood pressure, and/or normal cholesterol, and/or normal high sensitivity CRP, and/or normal blood lipids (e.g. triglycerides) etc. The subject may have a normal weight, or normal BMI parameters. In other embodiments the subject may be overweight or obese or have increased BMI parameters etc. In other embodiments, the subject may, as noted above, have low level inflammation, or chronic systemic inflammation, or age-related inflammation.

The treatment of inflammatory peripheral GnRH, or indeed any inflammatory condition, according to this aspect of the invention may involve a combination therapy as discussed above, and in particular a combination therapy with a sex hormone or other agent effective for hormone substitution therapy, and in particular the sex hormone or other agent may be titrated to baseline level or higher, as described above.

A method of the invention may accordingly involve determining a level of peripheral GnRH in a subject, and if said level is higher than that of a young healthy adult or 160 pg/ml or above, administering a GnRH antagonist.

The step of determining the peripheral GnRH level may involve monitoring the peripheral GnRH level in a subject over a period of time, e.g. over 1, 2, 3, 4, 5, 6, 8, 10, 12, 15, 18, 20 weeks or more, for example over 1, 2, 3, 4, 5, 6, 7, 8, 9 months or more, or 1, 2 or 3 years or more.

Accordingly, in some embodiments of the invention, the GnRH antagonist may be administered to a subject in whom the level of peripheral GnRH has been determined, in particular pre-determined, and in particular in a subject who has been monitored for peripheral GnRH levels. The uses of the invention may thus combine a step of determining or screening for peripheral GnRH levels and a step of administering a GnRH antagonist if the peripheral GnRH level exceeds a particular threshold or cut-off value (e.g. of 1600 pg/ml).

In another aspect, the invention provides a method for detecting or determining an inflammatory condition in a subject, said method comprising determining the level of peripheral GnRH in said subject. In particular such a method may, as discussed above, be performed on a sample of a body tissue or fluid e.g. serum or plasma. In other embodiments, as discussed above, an in vivo method, e.g. imaging or scanning may be used. In a particular embodiment the presence of an inflammatory condition is detected or determined if said level of peripheral GnRH is 160 pg/ml or more. In a particular embodiment, the subject may have low-level inflammation, or chronic systemic inflammation, or age-related inflammation. In other embodiments, the subject may be healthy or may have no signs or symptoms of an inflammatory disorder, as discussed above.

In a further aspect, the invention also provides an agent capable of disclosing GnRH level and/or activity for detecting or determining in vivo an inflammatory condition in a subject, Accordingly, in this aspect, the invention may provide a diagnostic method or use practiced on the body of the subject, i.e, agent for use in diagnosing an inflammatory condition in a subject. Such an agent may be a GnRH antgonist, or a molecule capable of binding to the GnRH receptor or to GnRH (e.g. an affinity binding partner for GnRH or for the GnRH receptor, such as antibody or fragment or derivative thereof), which antagonist or molecule is provided with a label, particularly a detectable label, e.g. a radiolabel or positron-emitting nuclide or some other signal-giving label.

EXAMPLES

The following examples are provided in order to demonstrate and further illustrate certain preferred embodiments and aspects of the present invention and are not to be construed as limiting the scope thereof.

Example 1

1. Baseline Demographics

| Variable | Patient 1 | Patient 2 | Patient 3 | Patient 4 | Patient 5 | Patient 6 |
|---|---|---|---|---|---|---|
| Age (years) | 56 | 58 | 45 | 71 | 78 | 71 |
| Sex | Female | Female | Premenopausal Female | Male | Female | Female |
| Disease Duration (years) | 10 | 26 | 17 | 16 | 31 | 38 |
| Disease activity[1] | 6.2 | 7.5 | 7.6 | 8.6 | 6.4 | 7.2 |
| Number of biologics previously failed | 6 | 7 | 5 | 3 | 1[2] | 5 |
| Onset ? | Menopause | Postpartum | Postpartum | Acute onset at the time of ear infection | Menopause | Postpartum |
| Duration/Effect of last biologic | 4 infusions Rituximab (Mabthera) (each 6 months apart). No effect. | 4 months. TNF-inhibitor (Simponi/ golilimumab) Increasing disease activity documented. | 1 infusion TNF-inhibitor (Remsima) Side effects. Increasing disease activity documented. | 1 infusion Rituximab (Mabthera) Increasing disease activity documented. | 2 infusions Rituximab (Mabthera) 6 months apart. Malignant melanoma diagnosis. Unknown effect on disease activity. | 2 months. Roactemra (Tocilizumab) Very low white cell count. Increased disease activity documented. |

[1]Measured by DAS-28. >5.1 defined as high
[2]Patient cannot use biologics (other than Rituximab), due to malignant melanoma.

Baseline and Final Visit Clinical Variables

| | Patient 1 | Patient 2 | Patient 3 | Patient 4 | Patient 5 | Patient 6 |
|---|---|---|---|---|---|---|
| Treatment duration (weeks) | 28 | 15 | 12 | 9 | 7 | 36 |
| Deagrelix loading dose, intervals, maintenance doses | 160 mg, Every 4 weeks to 3½ weeks, 80 mg | 180 mg, Every 4 weeks to 3½ weeks, 80 mg | 240 mg, Every 3½ weeks, 80 mg stepped up 120 mg | 240 mg, Every 3½ weeks, 80 mg stepped up to 160 mg | 120 mg, Every 5 weeks to 3½ weeks, 80 mg | 240 mg, Every 3½ weeks for 2 months, initially, then 80 mg every 2 weeks |
| ACR % Response | 90% | 60% | 50% | 50% | 30% | 80% |
| Swollen joint count assessed with ultrasound; baseline, final | 6, 0 | 17, 2 | 23, 4 | 24, 3 | 10, 2 | 16, 0 |
| Tender joint; baseline, final | 9, 0 | 17, 3 | 26, 11 | 28, 11 | 12, 0 | 24, 0 |
| Patient own assessment (0-100) | 81, 0 | 90, 35 | 50, 30 | 90, 50 | 88, 88[3] | 60, 7 |
| Physician assessment (0-100) | 85, 7 | 90, 40 | 90, 30 | 80, 40 | 70, 20 | 90, 7 |
| Function score (Good <1) | 1.25, 0 | 2.0, 0.25 | 1.75, 0.63 | 0.88, 0.38 | 1.29, 0.88 | 1.5, 0.625 |
| Morning stiffness (hrs) | 2.5, 0 | 9, 1 | 7, ½ | 7, 3 | 2.5, ¾ | 2, 0 |

[3]Muscular pain in arms

Baseline and Final Visit Laboratory Variables

| Laboratory variable (reference range)[4] | Patient 1 By 24 wks Baseline; Final | Patient 2 By 15 wks Baseline; Final | Patient 3 By 12 wks Baseline; Final | Patient 4 By 9 wks Baseline; Final | Patient 5 By 7 wks Baseline; Final | Patient 6 By 3½wks Baseline; Final |
|---|---|---|---|---|---|---|
| ESR (varies by age/sex) | 46, 24* | 51, 16* | 46, 20* | 78, 36 | 28, 8 | 37, 24* |
| CRP (<5) | 63, 16 | 44, 23 | 33, 19 | 142, 56 | <5, 6 | 22, <5* |
| CK (35-210) | 51, 61 | 25, 39* | 32, 55* | 18, 43* | 76, 61 | 74, 58 |
| Hb (varies by sex) | 12.2, 12.8 | 13.0, 13.3 | 11.4, 11.2 | 12.3, 12.8 | 11.4, 11.6 | 12.4, 13.2 |
| LH (varies by age/sex) | 22, <0. | 36, <0.3 | 2, >0.3 | 8, <0.3 | 44, <0.3 | 30, <0.3 |
| FSH (varies by age/sex) | 38, 1 | 72, 0.4 | 6, 1 | *15*, 0.7* | 64, <0.1 | 79, 0.6 |
| Homocysteine (5-17) | 10, 9 | 12, 13 | *31, 21* | 10, 10 | 10, 10 | 10, — |
| Rheumatoid factor (<14) | 7, 9 | *51, 38* | *178, 163* | *>200, >200* Above limit | *167, >200* | 8, 8 |
| CCP antibody (<10) | NEG, NEG | *101, 70* | *102, 101* | *>340, >340* Above limit | *257, 235* | NEG, NEG |
| HbA1C (4.3-6.1) | *6.4*, 6.1* | 5.3, 5.3 | 5.1, 5.4 | *6.9*, 6.4 | 5.1, 5.5 | 5.5, 5.4 |
| ACTH (<10.2) | *10.7*, 6.1* | 2.3, <1.1 | 3.9, 2.1 | 8.0, <1.1 | *11.3, 10.8* | <1.1, <1.1 |
| Blood Pressure | 151/90, 120/71* | 118/82, 126/80 | 110/68; 110/66 | 130/80; 120/78 | 134/79; 124/80 | 90/60; 100/64 |

[4]Italics denotes over reference range values, bold denotes under reference range values. ESR, erythrocyte sedimentation rate; CRP, C-reactive protein; CK, creatinine kinase; Hb, Hemoglobin; LH, luteinizing hormone; FSH, follicle-stimulating hormone; CCP, cyclic citrullinated peptide; HbA1C, glycated hemoglobin: ACTH, adrenocorticotrophic hormone Other Variables Including Safety Parameters

| Laboratory variable (reference range) | Patient 1 By 24 wks Baseline; Final | Patient 2 By 15 wks Baseline; Final | Patient 3 By 12 wks Baseline; Final | Patient 4 By 9 wks Baseline; Final | Patient 5 By 7 wks Baseline; Final | Patient 6 By 3½ wks Baseline; Final |
|---|---|---|---|---|---|---|
| ALAT (10-45) | 22, 26 | 14, 21 | 16, 23 | 52, 37 | 65, 52 | 18, 22 |
| Creatinine (varies with age/sex) | 56, 47 | 59, 59 | 42, 49* | 49, 56 | 20, 29 | 61, 46 |
| LDL (2.0-5.4) | 3.6, 3.8 | 2.8, 2.9 | 2.7, 2.3 | 2.7, 2.3 | 3.2, 3.2 | 2.2, 1.9 |
| HDL (1.0, 2.7) | 2.33, 2.31 | 1.93, 2.01 | 1.78, 1.42 | 1.78, 1.62 | 1.83, 1.64 | 1.71, 1.65 |
| Cholesterol (3.9-7.8) | 6.0, 6.3 | 5.0, 5.6 | 4.8, 4.5 | 4.8, 4.5 | 5.2, 5.4 | 4.3, 4.1 |
| Triglycerides (0.45-2.6) | 1.19, 1.38 | 1.16, 1.39 | 1.23, 1.38 | 1.23, 1.38 | 0.93, 1.06 | 1.21, 1.31 |
| P1NP (varies with sex) | 42, 43 | 33, 23 | 40, 38 | 39, 38 | 46, 35 | — |
| IGF-1 (varies with age) | 14.6, 12.0 | 19.1, 22.2 | 24.6, 25.9 | 24.6, 25.9 | 15.3, 12.0 | — |
| Osteocalcin (varies with sex) | 2.2, 3.8 | 4.7, 3.4 | 2.7, 3.3 | 3.3, 2.7 | 4.9, 4.4 | — |
| CTX-1 (varies with age and sex) | 0.42, 0.36 | 0.37, 0.31 | 0.65, 0.71 | 0.68, 0.83 | 0.48, 0.49 | — |
| Apo (A1) | 2.2, 2.2 | 2.0, 2.0 | — | — | — | — |
| Apo (B) | 1.1, 1.2 | 0.9, 0.9 | — | — | — | — |

*Denotes normalized values

The figures show differences before and after treatment with Degarelix. Patients have not increased their concomitant stable medications, and they have not intraarticular, intramuscular or intravenous cortisone therapy.

Patient 2 has returned to working part time and spinning hours at her local gym. She started 100% on sick benefits 3 years ago. Patient 3: Used crutches to come to the baseline consultation. She no longer requires crutches. FIGS. 1A, 1B and 1C show images of arthritis in the foot of patient 1 before and during treatment with Degarelix.

FIG. 2 shows ultrasound pictures of patient 5. FIG. 2A shows white area highlighted by arrow, is power Doppler denoting inflammatory activity in shoulder. FIG. 2 B shows no power Doppler in same shoulder. FIG. 2C shows white area highlighted by arrow, is power Doppler denoting inflammatory activity in right MCP 4 (finger joint) right side. FIG. 2D shows no power Doppler in right MCP4 joint. FIG. 2 E shows white area highlighted by arrow, is power Doppler denoting inflammatory activity in right MCP 4 (finger joint) left side. FIG. 2 F shows no power Doppler in MCP 4 left side, and decreased joint fluid (oval).FIG. 3 shows patient 6 before and after Degarelix treatment.

FIG. 4 shows ultrasounds of patient 6. The first ultrasound (left) shows a large effusion (swelling indicated by black area) over the right wrist. The second ultrasound (right) shows the same area by 3.5 weeks. The effusion on the right is much smaller, and no longer painful. She halved her long term stable prednisolone dose from 10 mg til 5 mg within days of the first Degarelix injection (without informing the physician). She has reduced two shoe sizes, bought new shoes, and also halved her morphine and diuretic intake ('Oxycodone/Oxynorm' and 'Butemanide/Burinex' tablets).

FIGS. 5A-F shows disease activity variables of Patient 2 whilst being treated with degarelix.

Example 2

Two examples of patients with continued RA improvement over several weeks despite stably low levels of LH Patient 3

| | Baseline | 4 wks | 8 wks | 12 wks |
|---|---|---|---|---|
| ACR % response | — | 30% | 40% | 50% |
| LH | 2 | <0.3 | <0.3 | <0.3 |
| ESR | 46 | 41 | 36 | 20 |

Patient 4

|  | Baseline | 3½ wks | 9 wks |
|---|---|---|---|
| ACR % response | — | 20% | 50% |
| LH | 8 | <0.3 | <0.3 |
| ESR | 78 | 68 | 36 |

Example 3

This Example Described the Treatment of Lupus with a GnRH Antagonist

Social History

A male, 63 years old, married with 3 grown up children has been on sick benefits since 2010 primarily due to lupus diagnosed in 1988.

History of Lupus

Figure 7A:
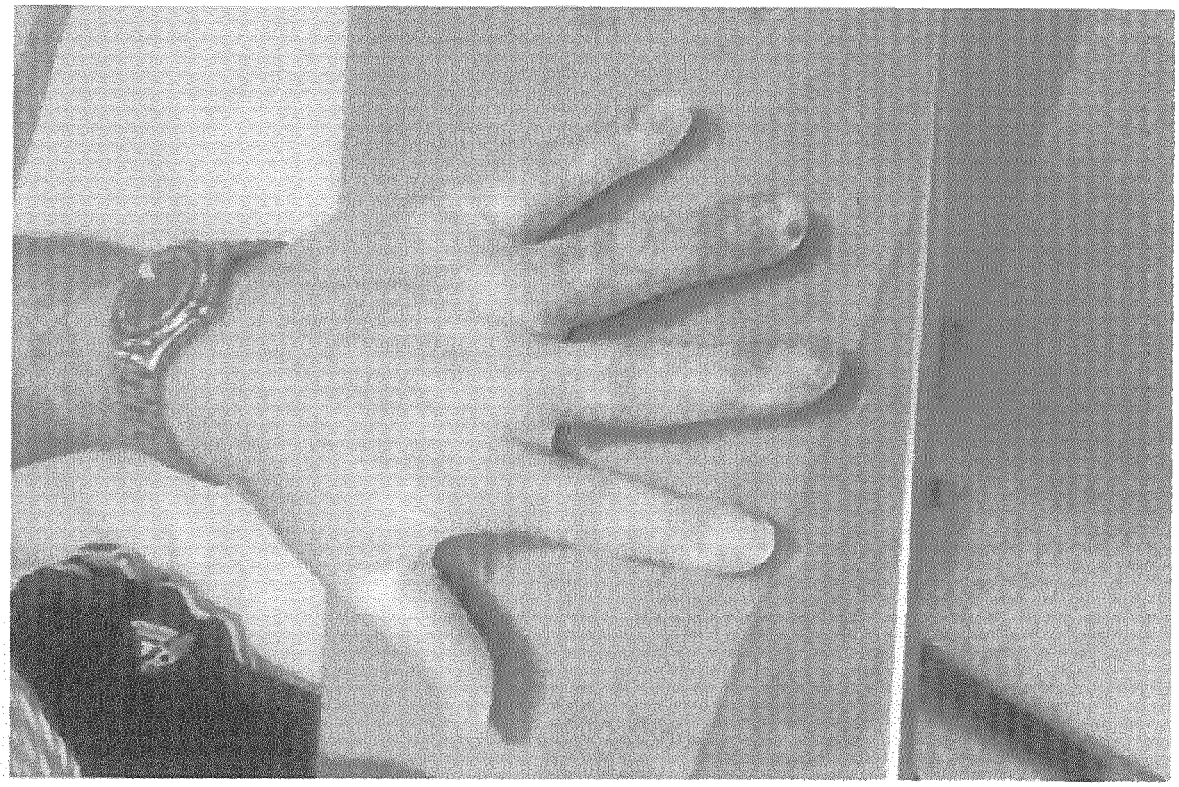
FIG. 7 shows hand ulcers in a lupus patient before A and after B degarelix treatment.
Figure 7B:
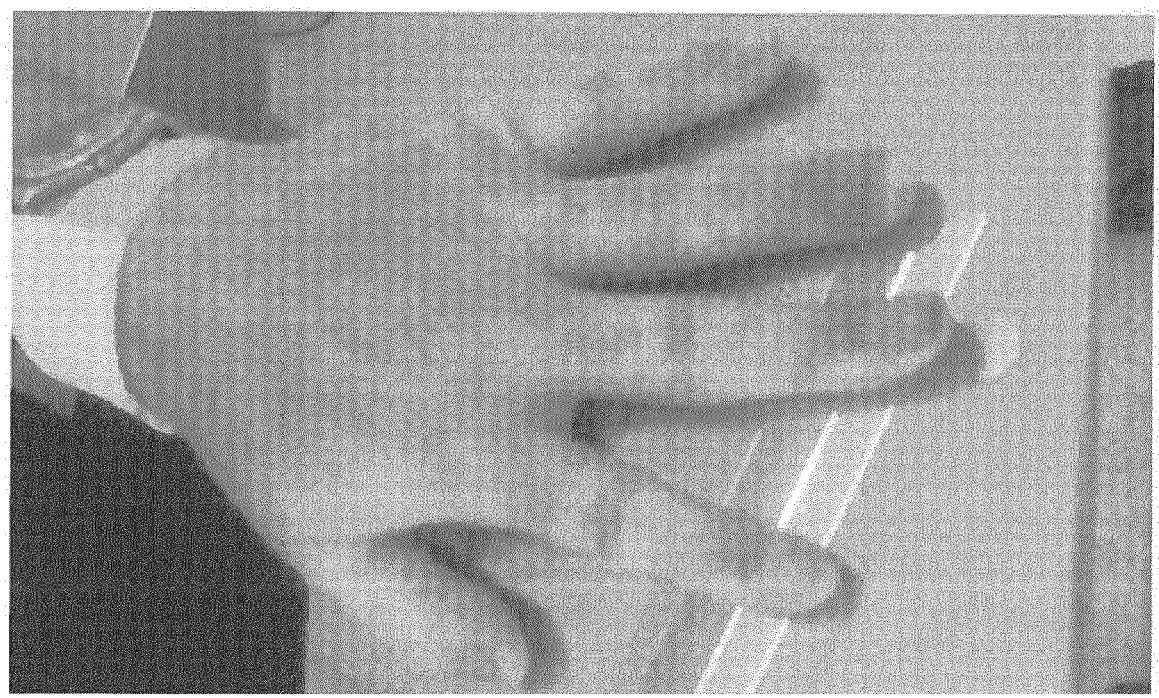
Figure 8:
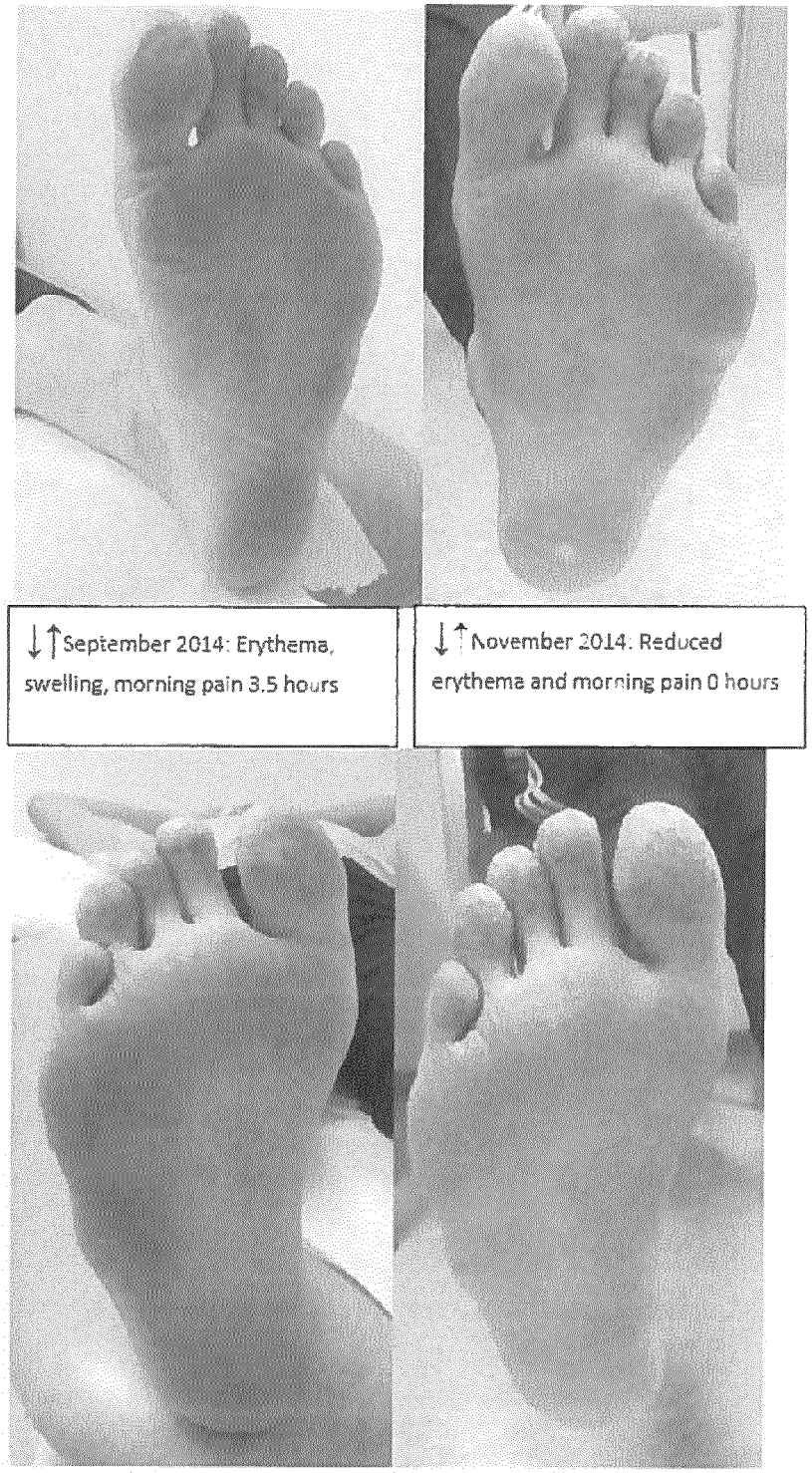
FIG. 8 shows photographs of foot swelling in a patient with lupus after 8 weeks of treatment with degarelix.

The patient has a medical history of a multimorbid patient. Systemic lupus erythematosus (SLE) was diagnosed in 1988 based on Raynauds, skin changes, arthralgia, high titre lupus anticoagulant, ANA, SSA, and SSB. Chilblain type changes in hands and feet (FIGS. 6-8). He has previously tried methotrexate, azathioprine, and mycophenolate mofetil, which were not effective in reducing the pain in his extremities, and gave intolerable side effects such as mouth ulcers. He has had a pacemaker since 1986, AV block II. The patient suffered cardiac arrest in 2012, coronary stenosis was observed. The patient had kidney failure since 2012, required dialysis, stabilized creatinine around 150, osteoporosis, COPD, and is a smoker.

The patient has had severe pain in his hands and feet for the last 10 years, especially under the soles of his feet. Has had continuous small ulcerations on his toes and hands, and pigmented skin. This pain was debilitating, and reduced his daily function. He walked with difficulty, and had atrophic musculature in both his lower extremities. He had ataxi in his lower extremities, especially left side, and minimal patellar and achilles reflexes. He was unbalanced, experienced numbness, and parasthesias, all documented in his medical journal from the neurology outpatients clinic April 2014. His electromyography findings from 2010 support a diagnosis of thin fiber neuropathy related to lupus. Due to his painful condition, he has been followed up by a pain clinic. He was offered a tricyclic antidepressant, amitriptyline 25 mg in March 2014 for his painful condition. This had no effect on his pain. In April 2014 the amitriptyline was increased to 50 mg with no effect. This was soon after increased to 150 mg daily with no effect. Thereafter he tried gabapentin 100 mg×3 up to 300 mg x 3 up to 1200 mg×3 with no effect. He has also tried oxycodone and naloxone 5/2.5 mg but this increased the pain. He has tried pregabalin up to 150 mg×2 with no effect.

By September 2014, we had no treatment options left. Therefore, we decided to offer him degarelix. GnRH antagonists have shown anti-inflammatory effects and therefore we considered that degarelix, a depot GnRH antagonist, may have a therapeutic effect in lupus.

Sep. 15, 2014, he received his loading dose of degarelix, 240 mg sc.

Assessment of Response

| Variable (ref range) | 15.09.14 | 23.09.14 | 14.10.14 | 07.11.14 |
|---|---|---|---|---|
| FSH (<12) | 14↑ | 2 | <0.1 | <0.1 |
| LH (<12) | 11 | <0.3 | — | <0.3 |
| ANA (<1) | >32↑ out of range | 31↑ (25.09.14) | 28↑ | 26↑ |
| Total urinary protein g/L | 0.78↑ (++ on urine sticks) | 0.75↑ (++ on urine sticks) | 0.15[2] | 0.17 |

Proteinuria decline is linked to improved lupus nephritis outcomes. Korbet et al studied 61 patients in a controlled trial comparing standard therapy with plasmapheresis for severe lupus nephritis. Of these, 34 patients attained a 50% or greater reduction at 6 months and 27 did not. The patient described in this case report obtained a complete remission of proteinuria by 1 month, which continues to be in remission at 2 months. He had constant, increasing proteinuria in 2014.

Figure 11:
FIG. 11 shows a photograph of a baseline of a patient with systemic sclerosis prior to treatment. 5 Digital ulcers/Pitting scars on finger pulpa and a fingertip pain score 100 mm (0-100 mm) was observed.

By day 10 of treatment, several ulcers had healed (FIGS. 6B, 6D, 7B, and 8B), and the patient noticed a remarkable improvement. By day 5 his morning pain had decreased from 3.5 hours to 1.5 hours; by day 10 to 0 hours. This continues to be at 0 hours by 8 weeks. The decreased swelling and erythema can be seen by day 10 and week 8 in FIG. 11. He told his physician he was able to walk without shoes, something he had not been able to do for several years.

By 1 month of treatment, the patient took a holiday in Poland, and was able to walk for several hours each day with the group he traveled with. He no longer has parasthesias and his balance has improved. He received his second dose of Degarelix in October 2014, 80 mg sc. He continues on 80 mg s.c. every two weeks.

This example demonstrates that Degarelix reduced several symptoms of lupus and increased quality of life in a lupus patient.

Example 4

The Example Describes the Treatment of Ankylosing Spondylitis with a GnRH Antagonist Social History 73 year old male, married. 2 grown up children. Previously worked as a welder. Prior to retirement, he was on 100% sick benefits since 1993; 50% since 1986.

History of Ankylosing Spondylitis

Diagnosed with ankylosing spondylitis in 1984, HLAB27 positive, with repeated iridocyclitis. Used non-steroidal anti-inflammatory drugs previously. He was offered the TNF-alpha inhibitor Golilimumab in 2010. His disease activity score was 8.9 in October 2010 (see below for explanation of disease activity score) on initiating Golilimumab; by the June 2012 this score had reduced to 6.6, but by May 2013 the effect had worn off and his score was 7.6. May 2013, he initiated Enbrel treatment, but his disease activity increased from 7.6 to 8.3. Due to his poor response to TNF-alpha therapy, he was offered the GnRH antagonist Degarelix in September 2014.

Assessment of Response

Disease activity in ankylosing spondylitis is measured by the BASDAI (Bath Ankylosing Spondylitis Disease Activity Index1), has been extensively validated in clinical trials, 2, 3 and is one of the most commonly used outcome measures in clinical trials. This is a composite index that evaluates fatigue, axial and peripheral pain, stiffness and enthesopathy. His BASDAI was at 8.7 at baseline. In September 2014 he received his first dose of Degarelix 240 mg sc. By 2 weeks, his BASDAI had reduced to 6.8, and by 6 weeks it had reduced to 5.8. This is the lowest BASDAI score he has ever had since we first started using this method of assessment 4 years ago in 2010. His morning stiffness lasted 4 hours at baseline, by 6 weeks his morning stiffness had reduced to 2 hours. He had his second dose of Degarelix 80 mg s.c in October 2014. Lumbar flexion and maximum arm abduction were increased after 6 weeks of treatment.

Response to therapy in clinical practice is defined as improvement of 2 units or 50% on a 0-10 scale of the BASDAI, and expert opinion that the treatment should be continued. His reduction by 6 weeks was 2.9 units, and 7.1 units with an 82% BASDAI score improvement by 9 weeks, and we shall continue treatment. A BASDAI 50% improvement is defined as a major clinical response. He has also achieved an ASAS 80 (Ankylosing Spondylitis Assessment Group of at least 80% improvement) response. For comparison, approximately 50-60% of patients achieve a BASDAI 50 by 12 weeks on TNF inhibitors (4). His ESR has decreased from 46 mm to 23 mm, which is his lowest ESR reading in 19 years. His serum urate has decreased from 515 to 426 umol/L, which is his lowest urate level also in 19 years. By 9 weeks of GnRH antagonist therapy, his kidney function has normalized, and fasting glucose reduced from 7.4 to 6.5 mmol/L. By 3 months, the effect on his ankylosing spondylitis remained, creatinine was at 98 umol/L, with a glomerular filtration rate of 66 ml/min/1.73 m2 in December 2014.

| Lab. Variable (Ref range.) | 10.09.14 | 24.09.14 | 27.10.14 | 10.11.14 |
|---|---|---|---|---|
| ESR <20 mm | 46↑ | 31↑ | 28↑ | 23↑ |
| CRP | <5 | <5 | <5 | <5 |
| Creatinine (60-105 umol/L) | 112↑ | 114↑ | 111↑ | 99 |
| Glomerular filtration rate (>60 ml/min/1.73 m²) | 56↓ | 55↓ | 56↓ | 65 |
| Urate (230-480 umol/L) | 515↑ | 512↑ | 495↑ | 426 |
| Glucose fasting (4.0-6.0 mmol/L) | 7.4 | — | — | 6.5 |

Past Medical History
1952 Operated as an 11 year old with a left hip replacement due to epiphysiolysis as a child.
1974 Cholecystectomy (gallbladder removal)
1982 Myocardial infarction, underwent coronary angiography where occlusion of the left anterior descending artery was shown.
1984 Diagnosed with ankylosing spondylitis, with repeated bouts of iridocyclitis in association with ankylosing spondylitis
1998 Left hip replacement for second time, right hip replacement; deep venous thrombosis
2009 Colitis, biopsy confirmed in 2010
2009 Carpal tunnel syndrome surgery in right hand; same in left hand 2010
2014 MGUS with M-component at 2.4 g/L
2014 Mild kidney failure References for Example 4

1 Garrett et al. A new approach to defining disease status in ankylosing spondylitis: The Bath Ankylosing Spondylitis Disease Activity Index (BASDAI) J Rheumatol 1994; 1: 2286-91.

2 Haywood et al. Patient-assessed health in ankylosing spondylitis: a structured review. Rheumatology 2005; 44:577-86.
3 Calin et al. Defining disease activity in akylosing spondylitis: is a combination of variables (Bath Ankylosing Spondylitis Disease Activity Index) an appropriate instrument? Rheumatology 1999; 38:878-82.
2. Rudwaleit M, et al. Prediction of a major clinical response (BASDAI 50) to tumour necrosis factor alpha blockers in ankylosing spondylitis. Ann Rheum Dis 2004; 63:665-670.

Example 5

Figure 9:
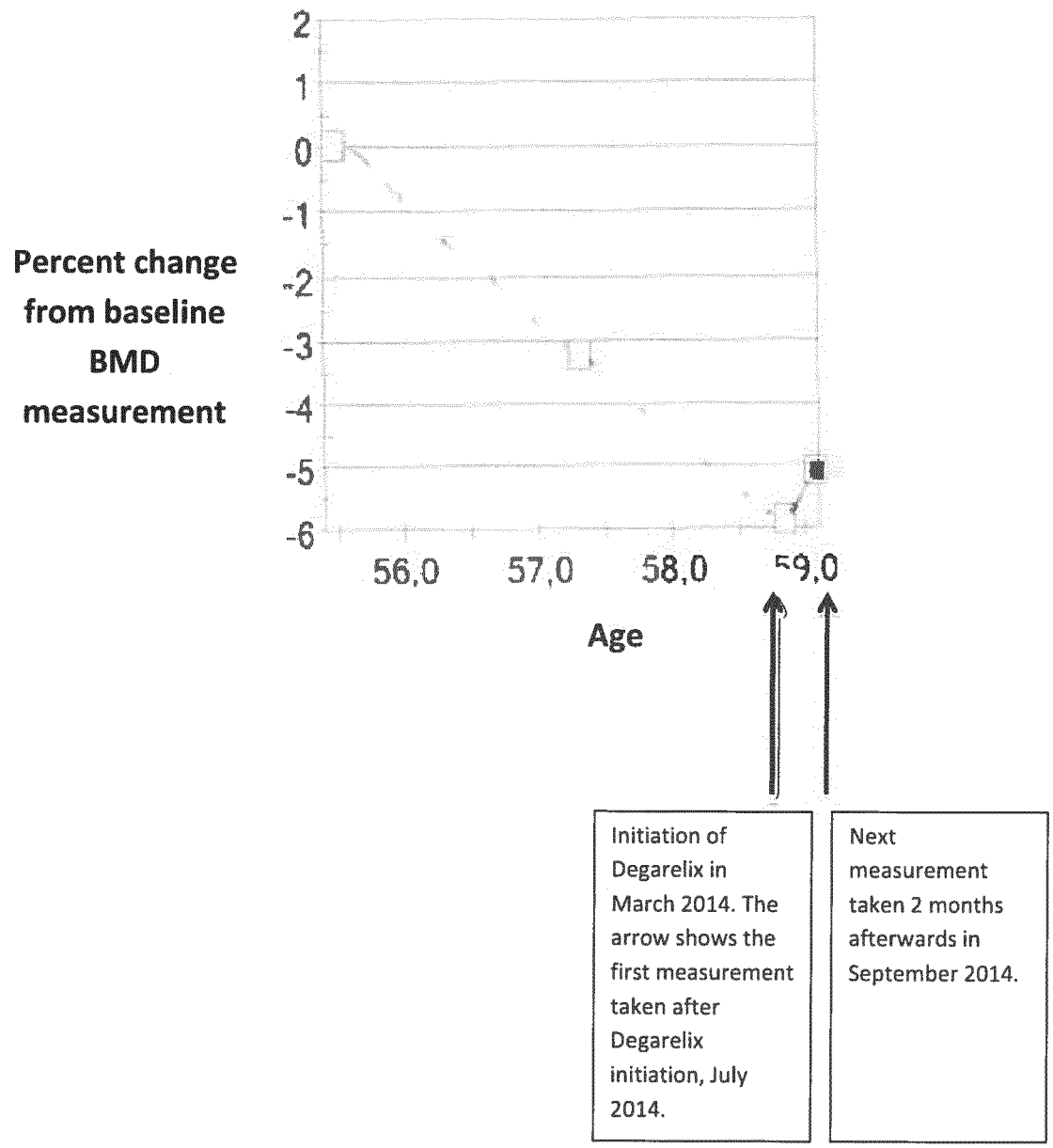
FIG. 9 shows hip bone mineral density in patient 1.

This Example Describes Improvement in Bone Mineral Density in Patients Taking a GnRH Antagonist Bone mineral density was measured in Patients 1 and 2 (See Example 1 for patient information). FIG. 9 shows that patient 1 shows an improvement in her bone mineral density in her hips for the first time in 3.5 years. She was not taking any therapies for osteoporosis during this period. This was unexpected as the summary of product characteristics states that a decrease in bone mineral density is expected under GnRH antagonist treatment. However, our data indicates the opposite. Despite having low oestrogen, using concomitant prednisolone and longstanding rheumatoid arthritis (all of which are independent risk factors for osteoporosis), her bone mineral density improved during GnRH antagonist treatment.

Figure 10:
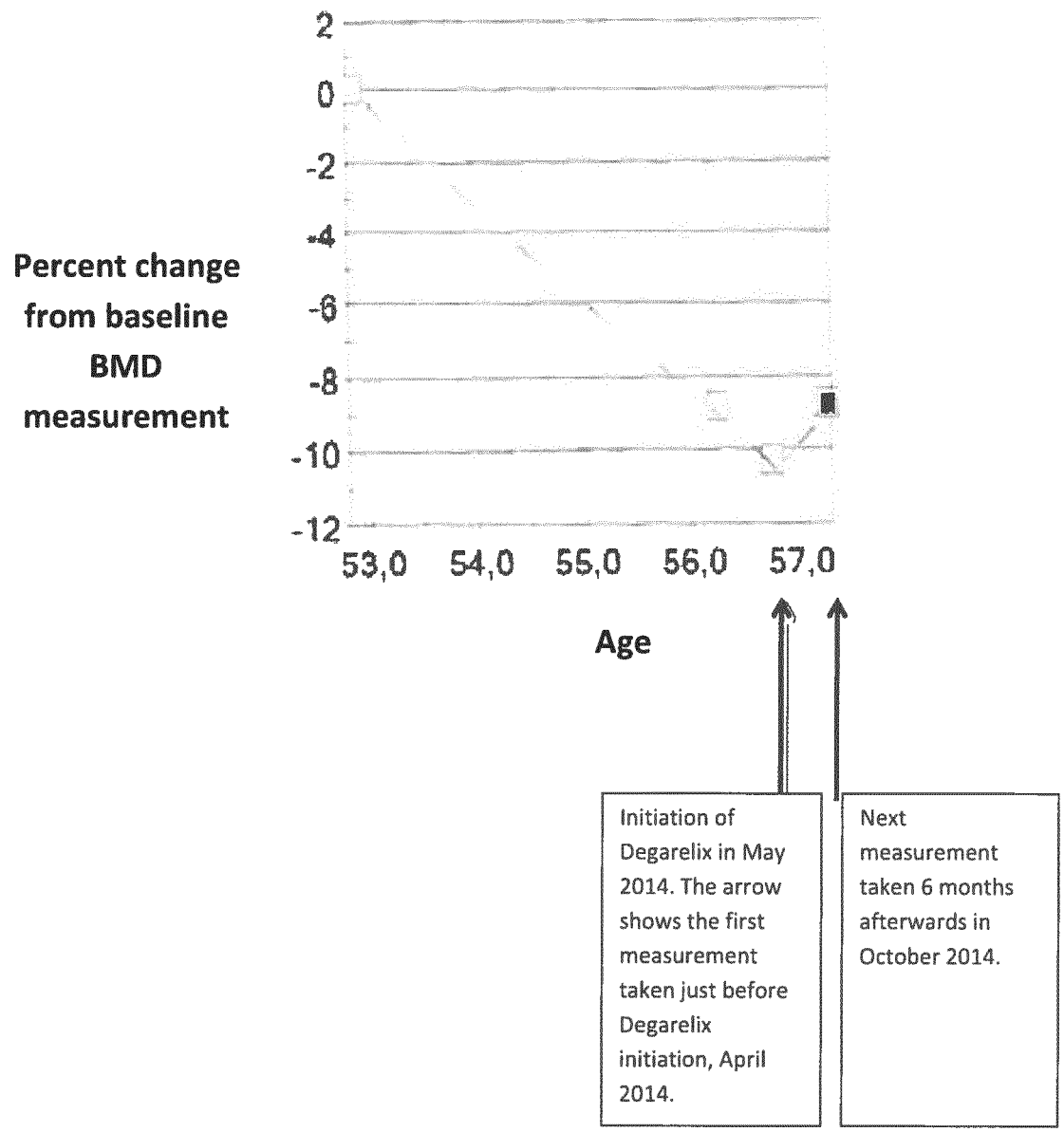
FIG. 10 shows hip bone mineral density in patient 2.

FIG. 10 shows an improvement in her bone mineral density in the hips of patient 2 for the first time in 4.5 years. This was unexpected as the summary of product characteristics states that a decrease in bone mineral density is expected under GnRH antagonist treatment. Despite using having low oestrogen, using concomitant prednisolone and longstanding rheumatoid arthritis (all of which are independent risk factors for osteoporosis), her bone mineral density improved during GnRH antagonist treatment.

Example 6

The summary of product characteristics for Degarelix states the following under section '4.4 Special warnings and precautions for use':
  Development or aggravation of diabetes may occur, therefore diabetic patients may require more frequent monitoring of blood glucose (and therefore HBA1c) when receiving androgen deprivation therapy.
  Cardiovascular disease such as stroke and myocardial infarction has been reported in the medical literature in patients with androgen deprivation therapy. Therefore, all cardiovascular risk factors should be taken into account.
Therefore it is unexpected that Degarelix could be beneficial in cardiovascular disease. However, our data below indicates this.

In our patient group who were offered Degarelix, some patients had risk factors for cardiovascular disease, metabolic syndrome, lipidemia or hypoalphalipoproteinemia (low HDL). None of these patients had recently started medications prior to the GnRH antagonist that could explain the changes in blood pressure, HbA1C, fasting glucose or lipids. See Example 1 for patient information.

Patient 1 with metabolic syndrome fulfilling 3 of 5 metabolic risk factors (large waistline >35 inches, high blood pressure and high fasting glucose). After degarelix treatment, she no longer fulfills the criteria for metabolic syndrome.

1. High HBA1c, contributes to CVD (normal reference range 4.3-6.1%) At baseline 6.4%, high. By 2 weeks HBA1c had normalized to 6.1%. This continues to be normal, and at 8 months is 5.7%. Her fasting glucose was 6.6 mmol/L in September 2014, by October 2014 this was reduced to 6.3 mmol/L.
2. High blood pressure, contributes to CVD at baseline 151/90 (measured at several times prior to baseline with repeatedly high blood pressure). Blood pressure by 6 months 120/71, and this continues to be normal. At her last check up at 8 months, her blood pressure was 118/78.
3. No other abnormalities at baseline for assessment Patient 4

High HBA1c, contributes to CVD (normal reference range 4.3-6.1%). At baseline the HBA1c was 6.9%, high. By 1 month the HBA1c had reduced to 6.6, by 2 months 6.4, and by 4 months 6.2, and by 12 months it was normalized to 5.9. His hospital records from a nearby hospital stated that his fasting glucose was high at 8.5 mmol/l (reference range 4.0-6.0) in December 2013, and by April 2014 this was higher at 8.9. They asked the patient's family doctor to initiate treatment due to the development of diabetes type II. His fasting glucose had reduced to 6.6 mmol/l by 3 months after starting Degarelix, and by 4 months has now normalised to 6.0 mmol/L. No other abnormalities baseline for assessment Patient 7

1. Low HDL, contributes to CVD (normal reference range 1.0-2.7 mmol/L). Mora et al investigated the link between cholesterol and cardiovascular events in women and found baseline HDL level was consistently and inversely associated with incident coronary and CVD events: A low HDL cholesterol level is thought to accelerate the development of atherosclerosis because of impaired reverse cholesterol transport and possibly because of the absence of other protective effects of HDL, such as decreased oxidation of other lipoproteins.

She had low HDL at baseline 0.68 mmol/L in September 2014. She received her loading dose of Degarelix 240 mg sc in September 2014. By 1 week, her HDL level had increased to 0.73, and by 2 weeks it continued to increase towards normal at 0.75. By 3 weeks it had normalized to 1.13 mmo/L and at 4 weeks is normal at 1.19 mmol/L.
2. No other abnormalities at baseline for assessment Patients 2, 3, 5, 6

These patients had no abnormalities (HBA1C, blood pressure, lipids) to indicate cardiovascular morbidity at baseline.

Example 7

Treatment of Inflammatory Bowel Disease

Patient History 73 year old male, diagnosed with colitis aged 69 yrs. Inflammatory bowel disease, colitis verified on colonic biopsy sample. Patients with inflammatory colitis usually have a higher incidence of autoimmune diseases. This patient also had ankylosing spondylitis.

Experimental Treatment

September 2014 received first dose of Degarelix 240 mg sc.

Received Degarelix 80 mg sc approximately every two weeks thereafter.

Assessment of Response

The inflammatory bowel diseases (IBD's), Crohn's disease and ulcerative colitis, are chronic relapsing, remitting disorders. The assessment of disease activity presents challenges to clinicians. Fecal biomarkers, such as fecal calprotectin, are a non-invasive method which can be used to aid managing clinicians. Calprotectin is released extracellularly in times of cell stress or damage and can be detected within feces and thus be used as a sensitive marker of intestinal inflammation. Fecal calprotectin has been shown to be useful in the diagnosis of IBD, correlates with mucosal disease activity, and can help to predict response to treatment or relapse. Fecal calprotectin levels are elevated in patients with both Crohn's disease and ulcerative colitis 1-2. There have been several studies looking at the use of fecal calprotectin to predict or monitor response to treatment.

In a study looking at 11 patients with relapsing IBD, fecal calprotectin was analysed at inclusion and after 8 weeks of treatment. Treatment was individualized medical therapy. A normalized fecal calprotectin concentration at 8 weeks predicted a complete response in 100% of patients,3 corresponding to endoscopic mucosal healing4. It has been shown that in patients with steroid induced clinical remission fecal calprotectin levels can remain elevated5-6. This finding is in keeping with earlier studies showing incomplete mucosal healing in patients treated with corticosteroids7.

Fecal calprotectin concentration decreases significantly at week 2 after an infliximab infusion (anti-tumour necrosis factor-α)8.

A level of <50 mg/kg is considered normal or remission for IBD.

This patient gave three fecal samples in total.

He started a GnRH antagonist 10 Sep. 2014.

| 3 samples in total | 24.09.14 | 02.10.14 | 10.01.15 |
|---|---|---|---|
| Fecal calprotectin mg/kg (<50 normal) | 79, high | 48, normal | 32, normal |

There is no gold standard index in the measurement of colitis disease activity in clinical trials. Due to the invasive nature of endoscopies, the Mayo non-invasive colitis assessment of response score can be used to assess treatment effect of IBD in clinical trials9-11. This score has been shown to correlate well with the total Mayo score 12. Both the partial Mayo and total Mayo score are used to assess disease activity in clinical trials13. The partial Mayo score also had good discriminatory value between subjects in remission and those with active disease14. A clinical response has been defined as a 3 point or greater change in the partial Mayo score15.

This patient had a partial Mayo score of 3 at baseline; and 0 at 12 weeks. A score of 0 is clinical remission. This is supported by his high fecal calprotectin score around baseline, reduced fecal calprotectin level at 4 weeks and further reduced calprotectin level by 12 weeks.

This example demonstrates GnRH antagonist treatment in a patient with colitis improved his disease activity, as well as normalizing his fecal calprotectin levels. As fecal calprotectin is high in IBD's in general, such as colitis and Crohn's disease, GnRH antagonists are beneficial in IBD's in general.

References for Example 7

[1] Røseth A G, et al. Assessment of disease activity in ulcerative colitis by fecal calprotectin, a novel granulocyte marker protein. Digestion 1997; 58: 176-180.
[2] Tibble J, et al. A simple method for assessing intestinal inflammation in Crohn's disease. Gut 2000; 47: 506-513.
[3] Wagner M, et al. Fecal markers of inflammation used as surrogate markers for treatment outcome in relapsing inflammatory bowel disease. World J Gastroenterol. 2008; 14: 5584-89.
[4] Roseth A G, et al. Normalization of fecal calprotectin: a predictor of mucosal healing in patients with inflammatory bowel disease. Scand J Gastroenterol 2004; 39: 1017-1020.
[5] Sipponen T, et al. Fecal calprotectin and lactoferrin are reliable surrogate markers of endoscopic response during Crohn's disease treatment. Scand J Gastroenterol 2010; 45: 325-331.
[6] Kolho K L, et al. Fecal calprotectin remains high during glucocorticoid therapy in children with inflammatory bowel disease. Scand J Gastroenterol 2006; 41: 720-725.
[7] Modigliani R, et al. Clinical, biological, and endoscopic picture of attacks of Crohn's disease. Evolution on prednisolone. Groupe d'Etude Therapeutique des Affections Inflammatoires Digestives. Gastroenterology 1990; 98: 811-818.
[8] Digestive Disease Week and the 107th Annual Meeting of the American Gastroenterological Association Institute, May 20-25, 2006, Los Angeles, Calif., USA. Abstracts. Gastroenterology 2006; 130: A1-911.
[9] Dhanda A D, et al. Can endoscopy be avoided in the assessment of ulcerative colitis in clinical trials? Inflamm Bowel Dis 2012; 18: 2056-62.
[10] Higgins P D, et al. Patient defined dichotomous endpoints for remission and clinical improvement in ulcerative colitis. Gut 2005; 54: 782-8.
[11] Higgins P D, et al. Is endoscopy necessary for the measurement of disease activity in ulcerative colitis? American Journal of Gastroenterology 2005; 100: 355-61.
[12] Lewis J D, et al. Use of the noninvasive components of the Mayo score to assess clinical response in ulcerative colitis. Inflamm Bowel Dis 2008; 14: 1660-66.
[13] Rutgeerts P, et al. Infliximab for induction and maintenance therapy for ulcerative colitis. N Engl J Med; 2005; 353: 2462-76.
[14] Turner D, et al. A systematic prospective comparison of noninvasive disease activity indices in ulcerative colitis. Clin Gastroenterol Hepatol 2009; 7: 1081-1088.
[15] Lewis J D, et al. Use of the noninvasive components of the Mayo score to assess clinical response in ulcerative colitis. Inflamm Bowel Dis 2008; 14: 1660-66.

Example 8

Treatment of Psoriasis

Patient History
  38 year old male, diagnosed with lithium induced psoriasis aged 26 yrs.
  His psoriasis was severe (erythema, induration and scaling), with a baseline Psoriasis Area Severity Index (PASI 1) score of 53.6. The PASI score is a standardized score for assessing disease activity in psoriasis.

Experimental Treatment

October 2014 received first dose of Degarelix 240 mg sc.
  He received Degarelix 80 mg sc every two weeks thereafter.
  His testosterone levels decreased from 12 nmol/L to <1 nmol/L (normal 8-35 nmol/L) after the first week of GnRH antagonist therapy. He therefore received testosterone supplementation in the form of Testogel containing 50 mg of testosterone, first daily; thereafter every 3 days to maintain testosterone levels within the normal range. At week 8 his testosterone levels were normalized at 9 nmol/L (under testosterone substitution and a GnRH antagonist.
Assessment of Response
  By 8 weeks his PASI score was 41.3; an absolute reduction of 12.3 points 23% reduction.
  This improvement in his psoriasis is stable at 6 months.
  High levels of serum uric acid in patients with psoriasis is a result of increased purine catabolism due to rapid epidermal cell turnover, and can be used as a marker of disease activity in psoriasis2. One study showed after 12 weeks of psoriasis treatment, mean values of serum uric acid were found to be significantly decreased in patients with psoriasis3.
  This patient had a serum uric acid (reference range 230-480 umol/L) of 485 umol/L at baseline; and this was normalized by 8 weeks at a level of 432umol/L.
  Lithium induced psoriasis is particularly resistant to therapy. There are very few trials of lithium induced psoriasis. One trial examined 15 patients with psoriasis who were taking lithium. Their psoriasis was mild, with a median pretreatment PASI score of 4.9. After 10 weeks of inositol therapy, their median PASI score was reduced by 1.7 points, or by 35% 4.
  The etiology of lithium induced psoriasis is uncertain, but may share some aspects with other types of psoriasis because lithium has also been reported to exacerbate existing psoriasis5. Due to the effect on lithium-induced psoriasis, with the decrease in serum uric acid levels which can be increased in psoriasis of any type, it is expected that GnRH antagonists will have a beneficial effect in psoriasis in general.
  This example demonstrates improved signs and symptoms in a patient with psoriasis treated with a GnRH antagonist treatment. This example also demonstrates the effective combination of a GnRH antagonist with gonadal hormone replacement, in this case testosterone replacement, in an inflammatory disease.

References for Example 8

[1] Fredsiksson T, et al. Severe psoriasis-oral therapy with a new retinoid. Dermatologica 1978; 157: 238-44.
[2] Jain V K, et al. C-reactive protein and uric acid levels in patients with psoriasis. Ind J Clin Biochem 2011; 26: 309-311.
[3] Jain V K, et al. C-reactive protein and uric acid levels in patients with psoriasis. Ind J Clin Biochem 2011; 26: 309-311.
[4] Allan S J R, et al. The effect of inositol supplements on the psoriasis of patients taking lithium: a randomized, placebo-controlled trial. Br J Derm 2004; M 150: 966-969.

[5]Skoven I, Thompson J. Lithium compound treatment and psoriasis. Arch Dermatol 1979; 115: 1185-7.

Example 9

Treatment of Systemic Sclerosis

Patient History
- 55 year old female, diagnosed with systemic sclerosis aged 52yrs.
- Fulfilled the 2013 EULAR/ACR classification criteria for systemic sclerosis1.
- Diagnosis based upon Raynauds phenomenon, positive ANA, high titre anti-Scl 70 antibodies, marked skin changes typical of scleroderma, and esophageal dysmotility.
- Previously tried Cyclophosphamide and Mycophenolate Mofetil.
- Progressive disease and worsening scleroderma skin features, despite therapy.
- Rapid progressive cardiac disease, verified by biopsy.

Experimental Treatment
- 5th December 2014 received first dose of Degarelix 240 mg sc.
- 9th January 2015 received second dose of Degarelix 80 mg sc.

Figure 12:
FIG. 12 shows a photograph of the same patient as FIG. 12 after 6 weeks of treatment. The fingers are almost cleared of digital ulcers/pitting scars on finger pulpa and the fingertip pain score is 30 (0-100 mm).
Figure 13:
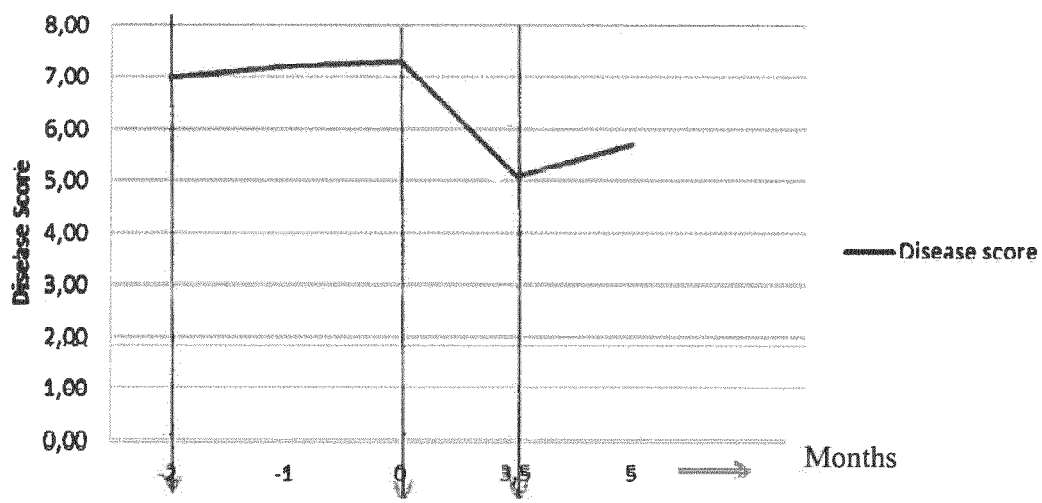
FIG. 13 shows the synergistic effect of methotrexate and GnRH antagonist in rheumatoid arthritis.

Assessment of Response at 6 weeks
- Digital ulcers and pitting scars are a characteristic feature of systemic sclerosis, contributing to disability and pain. They are important factors in patients' evaluations of quality of life2. Their precise objective evaluation can be included in randomized controlled trials3. Their pathogenesis is unclear. Histologically, there is a plug-like hyperkeratosis with parakeratosis, homogenized collagen fibers and perivascular mononuclear cell infiltration4. The improvement observed in this patient in the figures (FIGS. 12 and 13) was unexpected, as trials do not normally show a significant improvement in digital ulcers. For example, a trial with Cyclophosphamide showed that digital ulcers increased on average from 7 to 9 ulcers, over a period of 12 months5.
- Other measures of response to systemic sclerosis treatment include the Scleroderma Health Assessment Disease Activity Index and the associated Visual Analogue Scales, Table below Efficacy variables in a systemic sclerosis patient treated with a GnRH antagonist at baseline, 5 weeks and 6 weeks

|  | Baseline 5.12.14 | 5 weeks 09.01.15 | 6 weeks 19.01.15 |
| --- | --- | --- | --- |
| Modified Rodnan Skin Score | 42 | 40 | 40 |
| Digital tip ulcers/pitting scars | 5 | 2 | 2 |
| HAQ DI* | 1.88 | 1.38 | 1.38 |
| VAS** Pain | 100 | 10 | 10 |
| VAS Fingertip pain/pitting scars/ulcers | 100 | 40 | 30 |
| VAS Raynauds/vascular | 100 | 40 | 30 |
| VAS Global | 100 | 40 | 40 |
| VAS Lung/dyspnea | 100 | 80 | 50 |
| VAS Fatigue | 100 | 75 | 60 |
| VAS Gastrointestinal Symptoms | 100 | 80 | 60 |
| Sleep | 2 hrs/night | 5 hrs/night | 5.5 hrs/night |

*HAQ DI, Health Assessment Questionnaire Disease Index;
**VAS, Visual Analogue Scale This example demonstrates improved signs and symptoms in a patient with systemic sclerosis treated with a GnRH antagonist.

References for Example 9

[1]Van den Hoogen, et al. 2013 Classification Criteria for systemic sclerosis. Arthritis & Rheum 2013; 65: 2737-47.
[2]Malcarne V L, et al. Medical signs and symptoms associated with disability pain and psychological adjustment in systemic sclerosis. J Rheumatol 2007; 34: 359-67.
[3]Amanzi L, et al. Digital ulcers in scleroderma: staging characteristics and sub-setting through observation of 1614 digital lesions. Rheumatology 2010; 49:1374-82.
[4]Maeda M, et al. Pitting scars in progressive systemic sclerosis. Dermatology 1993; 187: 104-8.
[5]Au K, et al. Course of dermal ulcers and musculoskeletal involvement in systemic sclerosis patients in the scleroderma lung study. Arthritis Care Res 2010; 62: 1772-8.
[6]Steen V D, et al. The value of the Health Assessment Questionnaire and special patient-generated scales to demonstrate change in systemic sclerosis patients over time. Arthritis Rheum 1997; 40: 1984-91

Example 10

Treatment of Rheumatoid Arthritis Using Cetrorelix

Patient History
- 50 year old female with seropositive rheumatoid arthritis with disease duration of 10 years.
- Fulfilled ACR 2010 classification criteria for rheumatoid arthritis.

Experimental Treatment
- Had tried all therapies available previously without effect.
- Offered experimental GnRH antagonist therapy, Cetrorelix in 0.5 mg sc daily in October 2014, then 0.75 mg sc daily in December 2014.

Assessment of Response at 12 Weeks
- Disease activity score (DAS) reduction from 6.1 to 5.5.
- A DAS reduction of 0.6 units is defined as a clinical response to treatment.
- Her ESR normalized from 35 mm to 28 mm, with a decrease in her CRP from 41 mg/L to 18 mg/L. Her rheumatoid factor level has also decreased from 137kIU/L to 111 kIU/L.

This example demonstrates that Cetrorelix, a GnRH antagonist, improved signs and symptoms in a patient with rheumatoid arthritis.

Example 11

Example of a Patient with Spondyloarthritis

Patient History
- 38 year old male, diagnosed with spondyloarthritis aged 38 yrs.
- Fulfilled the ASAS criteria for axial radiographic spondyloarthritis.

Experimental Treatment

October 2014 received first dose of Degarelix 240 mg sc.

Received Degarelix 80 mg sc every two weeks thereafter.

Assessment of Response

Disease activity in ankylosing spondylitis/spondyloarthritis is measured by the BASDAI (Bath Ankylosing Spondylitis Disease Activity Index[1]), has been extensively validated in clinical trials[2-3], and is one of the most commonly used outcome measures in clinical trials. This is a composite index that evaluates fatigue, axial and peripheral pain, stiffness and enthesopathy. His BASDAI was at 3.8 at baseline. In October 2014 he received his first dose of Degarelix 240 mg sc. By 2 weeks, his BASDAI had reduced to 2.9, and by 8 weeks it had reduced to 1.3, remission. At 4 months, his BASDAI continues to be low at 1.5.

Response to therapy in clinical practice is defined as improvement of 2 units or 50% on a 0-10 scale of the BASDAI, and expert opinion that the treatment should be continued. His reduction by 4 moths was 2.3 we shall continue treatment.

This example demonstrates improved signs and symptoms in a patient with spondyloarthritis treated with a GnRH antagonist.

References for Example 11

[1]Garrett et al. A new approach to defining disease status in ankylosing spondylitis: The Bath Ankylosing Spondylitis Disease Activity Index (BASDAI) J Rheumatol 1994; 1: 2286-91.

[2]Haywood et al. Patient-assessed health in ankylosing spondylitis: a structured review. Rheumatology 2005; 44:577-86.

[3]Calin et al. Defining disease activity in akylosing spondylitis: is a combination of variables (Bath Ankylosing Spondylitis Disease Activity Index) an appropriate instrument? Rheumatology 1999; 38:878-82.

Example 12

Treatment of Multiple Sclerosis

Patient History 58 year old female, diagnosed with multiple sclerosis (MS) aged 50 years. Her MS was of the progressive type; characterized by a steady deterioration in function.

Fulfilled the 2010 McDonald Criteria for the diagnosis of MS 1.

Experimental Treatment

So far results of clinical trials for progressive MS have generally been disappointing. Currently, there is no FDA approved treatment for progressive MS disease.

December 2014 received first dose of Degarelix 240 mg sc.

Received Degarelix 80 mg s.c every two weeks thereafter.

Difficulties in Assessing Response in Progressive MS

Almost all trials in progressive MS show a worsening in function over time. The primary endpoint of these trials is usually to be able to show less worsening in the active treatment group compared to the placebo/other treatment group. Worsening is often defined as an increase in the Expanded Disability Status Scale (EDSS). EDSS is severely restrictive as an outcome measure for trials in progressive sclerosis.[2] Trials have not shown improvements in the EDSS or function in MS patients.[2] Optimal outcome measures in progressive MS are open to debate.

Effective imaging outcomes in clinical trials have allowed for the development of treatments for the relapsing-remitting type of MS. Unfortunately, similar outcomes do not exist in progressive MS. One of the most important factors in choosing outcome measures for these patients is the meaningfulness to patients.

Assessment of Response at 6 Weeks

General Function:

The patient reported a general improvement in her function, with the ability to be able to use her MS affected lower limbs better than she had been able to in the past 1 year, with continuing gradual improvement under GnRH antagonist treatment. This was particularly evident in her ability to raise her feet onto a step, physiotherapy exercises, and dressing. In the past year, she previously had always required her husband's help to climb a step at home, or to carry out certain lower limb exercises with her physiotherapist. By 4 weeks of GnRH antagonist treatment, she no longer required her husband's help/physiotherapist's help to perform these activities. She climbed onto a step unaided at her 6 week checkup. The improvement started at around 4 weeks after the initiation of therapy, and continued to improve further by 6 weeks.

Expanded Disability Status Scale (EDSS):

This patient's EDSS has remained stable at 6.5, as expected over such a short time period of 6 weeks. A score of 6.5 is equivalent to only being able to walk with the aid of a walker, as in her case. This was evident at baseline and 6 weeks.

Multiple Sclerosis Impact Scale 29 (MSIS-29):

Patient-reported outcomes are of increasing importance in trials of progressive multiple sclerosis.[2]The most frequently used global patient-reported outcome in multiple sclerosis is the MSIS-29.[3] This has been correlated with clinical and imaging metrics specifically in progressive forms of the disease.[4] According to a recent review,[2] patient reported outcomes in trials of progressive multiple sclerosis can be used to validate MRI or clinical metrics, and increased use of patient-reported outcomes in trials of progressive multiple sclerosis will expected to help satisfy regulators' requirements that treatments show relevant benefit for patients.

At baseline, she scored 121 on the MSIS-29. By 6 weeks, her score was reduced to 110. A clinically significant minimal difference is a score change of 8. Therefore this reduction of 11 in her score is considered clinically significant.[5]

Multiple Sclerosis Walking Scale-12 (MSWS-12)

The MSWS-12[6] was designed as a disease-specific patient-based instrument for use in clinical trials and clinical practice, to capture the complex impact of MS on walking ability. The MSWS-12 has been extensively evaluated in MS, with demonstration of internal consistency, high reliability and validity, and good generalizability.[7,8] A strong correlation between the MSWS-12 and accelerometer counts was observed,[9] suggesting a measurable relationship between objective mobility and a patient' perception of his or her walking ability. One of the most important attributes of the MSWS-12 in comparison to other assessments of walking in MS patients, is its responsiveness to change. During validations, the MSWS-12 was shown to be more responsive than other walking based measures, including the EDSS and the timed 25 foot walk (T25FW).

At baseline, she scored 60 on the MSWS-12. By 6 weeks, her score was reduced to 53. This is a 12% improvement. A minimal clinically significant difference has not yet been established.

Modified Fatigue Impact Scale for Multiple Sclerosis-5 Item Version (MFIS-5)

The MFIS-5 is a modified form of the Fatigue Impact Scale[10] based on items derived from interviews with MS patients concerning how fatigue impacts their lives. This instrument provides an assessment of the effects of fatigue in terms of physical, cognitive, and psychosocial functioning.

At baseline, she scored 20 on the MFIS-5. By 6 weeks, her score was reduced to 12. This was a reduction of 40%, which is clinically significant.

Timed 25 Foot Walk (T25FW)

The T25FW is another common endpoint in trials. At baseline, she used 16.7 seconds to walk 25 feet, and by 6 weeks she used 15.2 seconds. This improvement in walking speed supports the patient's reported improved outcomes.

The significant improvement in the MSIS-29 is supported by her significantly improved fatigue in the MFIS-5, her improvement in the MSWS-12, shorter T25FW time, and stable EDSS. This example demonstrates improved signs and symptoms in a patient with MS treated with a GnRH antagonist. This improvement in progressive MS is likely to also be observed in the relapsing-remitting type of MS. This is because the relapsing-remitting type gives similar signs and symptoms as the progressive type to patients over time.

References for Example 12

[1] Polman C H, et al. Dignostic criteria for multiple sclerosis: 2010 revisions to the McDonald Criteria. Ann Neurol 2011; 69: 292-302.

[2] Ontaneda D, et al. Clinical trials in progressive multiple sclerosis: lessons learned and future perspectives. Lancet Neurol 2015; 14: 208-23.

[3] Hobart J, et al. The multiple sclerosis impact scale (MSIS-29): a new patient-based outcome measure. Brain 2001; 124: 962-73.

[4] Hayton T, et al. Clinical and imaging correlates of the multiple sclerosis impact scale in secondary progressive multiple sclerosis. J Neurol 2012; 259: 237-45.

[5] Costellow L, et al. The patient knows best: Significant change in the physical component of the Multiple Sclerosis Impact Scale (MSIS-29 physical). J Neurol Neurosurg Psychiatry 2007; 78: 841-844.

[6] Hobart J C, et al. Measuring the impact of MS on walking ability: the 12-Item MS Walking Scale (MSWS-12). Neurology 2003; 60: 31-36.

[7] Motl R W, et al. Confirmation and extension of the validity of the Multiple Sclerosis Walking Scale-12 (MSWS-12). J Neurol Sci 2008; 268: 69-73.

[8] McGuigan C, et al. Confirming the validity and responsiveness of the Multiple Sclerosis Walking Scale-12

[9] Motl R W, et al. Confirmation and extension of the validity of the Multiple Sclerosis Walking Scale-12 (MSWS-12). J Neurol Sci 2008; 268: 69-73.

[10] Fisk J D, et al. Measuring the functional impact of fatigue: initial validation of the fatigue impact scale. Clin Infect Dis 18 Suppl 1: S79-831994.

Examples 13 and 14 Describe the Treatment of RA Using Particularly Different Dosing Schedules Example 13

Treatment Using Degarelix 40 mg Weekly

Patient History
  57 year old female with seropositive rheumatoid arthritis with disease duration of 22 years.
  Fulfilled ACR 2010 classification criteria for rheumatoid arthritis.
Experimental Treatment
  Had tried most therapies available (for example: Humira, Remicade, Enbrel, Actemra, several disease modifying anti-rheumatic drugs), previously without effect or intolerable side effects.
  Offered experimental GnRH antagonist therapy, Degarelix 40 mg every week with 240 mg loading dose at baseline.
Assessment of Response
  Disease activity score (DAS) reduction from 7.3 to 6.7 at 2 weeks.
  A DAS reduction of 0.6 units is defined as a clinical response to treatment (1).
  Her ESR has decreased from 62 mm to 38 mm, with a decrease in her CRP from 87 mg/L to 67 mg/L.

This example demonstrates that Degarelix, a GnRH antagonist, given as 240 mg loading dose with 40 mg weekly thereafter, improved signs and symptoms in a patient with rheumatoid arthritis.

Reference for Example 13

1. Van Gestel A M, et al. Development and validation of the European League Against Rheumatism response criteria for rheumatoid arthritis. Arthritis Rheum 1996; 39: 34.40.

Example 14

Treatment Using Ganirelix

Patient History
  50 year old female with seropositive rheumatoid arthritis with disease duration of 10 years.
  Fulfilled ACR 2010 classification criteria for rheumatoid arthritis.
Experimental Treatment
  Had tried almost all available rheumatoid arthritis therapies available previously without effect.
  Offered experimental GnRH antagonist therapy, Ganirelix 0.75 mg sc daily (0.25 mg sc three times a day)
Assessment of Response at 4 Months
  Disease activity score (DAS) reduction from 5.5 to 2.2 (remission).
  A DAS reduction of 0.6 units is defined as a clinical response to treatment (1).
  Her ESR decreased from 28 mm to 19 mm, with a normalization of her CRP from 23 mg/L to 5 mg/L. This is supported by the decrease in her anti-cyclic citrullinated peptide (CCP) antibodies from 27 u/mL. to 14 u/mL. Her rheumatoid factor level has also decreased from 113 kIU/L to 75 kIU/L.

This example demonstrates that Ganirelix, a GnRH antagonist, improved signs and symptoms in a patient with rheumatoid arthritis.

Reference for Example 14

1. Van Gestel A M, et al. Development and validation of the European League Against Rheumatism response criteria for rheumatoid arthritis. Arthritis Rheum 1996; 39: 34.40.

Example 15

Example of Treatment Using the Oral GnRH Antagonist Elagolix

Patient History
  56 year old female with seropositive rheumatoid arthritis with disease duration of 10 years.
  Fulfills ACR 2010 classification criteria for rheumatoid arthritis.
Experimental Treatment
  Is offered experimental GnRH antagonist therapy, Elagolix 550 mg daily for 12 weeks.
Assessment of Response at 4 Months
  Disease activity score (DAS) is reduced with over 0.6 units.
  A DAS reduction of 0.6 units is defined as a clinical response to treatment (1).
  This example demonstrates how Elagolix, a GnRH antagonist, can improve signs and symptoms in a patient with rheumatoid arthritis shown with international response criteria.

Reference for Example 15

1. Van Gestel A M, et al. Development and validation of the European League Against Rheumatism response criteria for rheumatoid arthritis. Arthritis Rheum 1996; 39: 34.40.

Example 16

Example Treatment Using the Oral GnRH Antagonist Relugolix

Patient History
  56 year old female with seropositive rheumatoid arthritis with disease duration of 10 years.
  Fulfills ACR 2010 classification criteria for rheumatoid arthritis.
Experimental Treatment
  Is offered experimental GnRH antagonist therapy, Relugolix 250 mg daily for 12 weeks.
Assessment of Response at 4 Months
  Disease activity score (DAS) is reduced from 3.5 to 2.5 (remission), or a Good Eular Response
  A DAS reduction of 0.6 units is defined as a clinical response to treatment (1).
  This example demonstrates that Relugolix, a GnRH antagonist, improves signs and symptoms in a patient with rheumatoid arthritis.

Reference for Example 16

1. Van Gestel A M, et al. Development and validation of the European League Against Rheumatism response criteria for rheumatoid arthritis. Arthritis Rheum 1996; 39: 34.40.

Example 17

Example Treatment Using the Oral GnRH Antagonist ASP1707

59 year old female with seropositive rheumatoid arthritis with disease duration of 8 years.
  ASP1707 7.5 mg daily for 12 weeks.
Assessment of Response at 4 Months
  Disease activity score (DAS) is reduced with over 0.6 units.
  A DAS reduction of 0.6 units is defined as a clinical response to treatment (1).
  This example demonstrates how ASP1707, a GnRH antagonist, improves signs and symptoms in a patient with rheumatoid arthritis shown with international response criteria.

Reference for Example 17

1. Van Gestel A M, et al. Development and validation of the European League Against Rheumatism response criteria for rheumatoid arthritis. Arthritis Rheum 1996; 39: 34.40.

Example 18

Example of Screening, Diagnosis, and Treatment of Age Related Inflammation

A randomized controlled trial is carried out to ascertain whether inhibiting the effects of GnRH reduces fracture rates, vascular events, myocardial infarctions, and all-cause mortality, with or without gonadal hormone replacement. In a randomized controlled trial approximately 3000 men and 3000 women or more, who have moderate peripheral GnRH levels or levels above 160 pg/mL are allocated to three groups: to either daily oral 5500 mg Elagolix, oral 5500 mg Elagolix combined with oestrogen (for example, Activelle 1 mg/0.5 mg women or the amount required to titrate to age/sex pre-chosen levels) or testosterone (for example, Testogel 50 mg every 2-3 days for men or the amount required to titrate to age/sex pre-chosen levels) or placebo. All participants are followed prospectively for the primary trial end point of first-ever myocardial infarction, stroke, hospitalization for unstable angina, arterial revascularization, bone fracture, or cardiovascular death. All analyses are performed on an intention-to-treat basis. Additional analyses include evaluations of total mortality; the number needed to treat (NNT) to prevent 1 vascular event; whether any observed effect is attributable to LDL reduction, to CRP reduction, or to a combination of both lipid-lowering and antiinflammatory effects. After follow up of 5 years there is a significant reduction in the trial primary end point of vascular events, a reduction in myocardial infarction, and a reduction in all-cause mortality in the Elagolix combination with gonadal replacement group compared to placebo.

This example demonstrates how one could potentially screen for age related inflammation/systemic inflammation, and treat or prevent it with a drug that lowers the effects of GnRH.

Example 19

Example of Preventing Age Related Inflammation

An animal study is conducted with 40 fertile female mice aged approximately 6-20 months in a control group (group 1) receiving placebo, 40 age and sex matched mice receiving a drug that reduces the activity of GnRH (group 2), such as Cetrorelix 0.5 mg/kg daily, and 40 age and sex matched mice receiving the same GnRH inhibitor as group 2, but with the additional replacement of gonadal hormone (oestrogen) to age adjusted pre-chosen levels. All mice are followed prospectively, and evaluated for systemic inflammation markers, atherosclerosis, osteoporosis, LDL, and age at death. The same three interventions and assessments are carried out in three groups of male mice with 40 male mice in each group, aged approximately 6-20 months, replacing the gonadal hormone testosterone to pre-chosen levels in group 3. Mice treated with a drug that reduces the activity of GnRH, such as Cetrorelix 0.5 mg/kg daily with or without the replacement of gonadal hormone (preferably with) reach a higher age at death compared with mice in the placebo groups. These mice also show less atherosclerosis, osteoporosis and systemic inflammation than mice in the placebo groups.

This example demonstrates how a drug to lower the effects of GnRH, such as Cetrorelix can be given to prevent and/or treat age related inflammation.

Example 20

Example to Demonstrate Synergistic Effect of GnRH Antagonism with a Disease Modifying Drug, Such as Methotrexate, in Rheumatoid Arthritis Patient History
  71 year old male with seropositive rheumatoid arthritis with disease duration of 16 years
  Fulfilled ACR 2010 classification criteria for rheumatoid arthritis
Experimental Treatment and Assessment of Response
  Previously failed 3 biologics (Etanercept, Actemra, and Rituximab). Last tried Rituximab November 2013, but increasing disease activity and blood tests (CRP and ESR) during the months thereafter until start of Degarelix 16 Jun. 2014. Concomitantly used stable Methotrexate 10 mg weekly since 1999.
  Started Degarelix 240 mg inductions dose 16 Jun. 2014, with 80 mg every 2 weeks thereafter.
  Disease activity reduced and he achieved an ACR60 response by 29 Sep. 2014 under the introduction of Degarelix and stable concomitant Methotrexate and Prednisolone.
  3 Oct. 2014 the patient's pulmonary physician stopped Methotrexate treatment due to pleural thickening, and CT imaging supporting lung fibrosis which was suspected to be due to Methotrexate. The patient had dyspnea which resolved once Methotrexate was stopped.
  By 21 Nov. 2014, the patients disease activity score had increased from 5.1 (29 Sep. 14) to 5.7 (21 Nov. 2014), due to the discontinuation of Methotrexate.

This example demonstrates that the combination of GnRH antagonist treatment with a DMARD (disease modifying drug) such as Methotrexate improves signs and symptoms in rheumatoid arthritis.

Example 21

Background/Purpose

Gonadotropin-releasing hormone (GnRH) agonists lead to increases in the bone formation marker, procollagen type 1 amino-terminal propeptide (P1NP), due to increased bone turnover, followed by decreased bone mineral density (BMD).[1]

The effect of GnRH antagonists on bone metabolism is thought to be similar, as both drugs paradoxically lead to estrogen deprivation. However, data is lacking. We investigated the short-term effects of a GnRH-antagonist, cetrorelix (which rapidly decreases luteinizing hormone [LH] and follicle-stimulating hormone [FSH]), on levels of P1NP.
Methods:

In this double-blinded, single-site study in Norway (ClinicalTrials.gov NCT00667758), 99 patients with active longstanding RA, were randomised to predefined intention-to-treat populations using computer-generated allocation (1:1) in dynamic blocks stratified for sex. Patients were assigned to subcutaneous cetrorelix (n=48) (5 mg days 1-2, 3 mg days 3-5) or placebo (n=51). P1NP was measured on day 10. We investigated serum P1NP between groups, a predefined secondary endpoint. Detailed efficacy and safety data are presented separately.
Results:

P1NP (µg/L) was significantly reduced in the cetrorelix group (−4.21) compared with the placebo group (mean difference −0.57 and −3.45 respectively [95% CI:−6.62; −0.29], p=0.033) by day 10; following significant reductions in disease activity markers and TNF-α (log pg/mL). Adverse event rates were similar between groups.
Conclusion:

This study demonstrates antagonizing GnRH with cetrorelix decreases P1NP, suggesting decreased bone turnover, as well as reductions in disease activity and TNF-α. This is in contrast to observed increases in P1NP with GnRH agonist therapy. Further studies regarding the effect of upstream hypothalamic-pituitary-gonadal axis hormones on bone metabolism are warranted.

Reference for Example 20

Smith et al. Raloxifene to prevent gonadotropin-releasing hormone agonist-induced bone loss in men with prostate cancer: A randomized controlled trial. Journal of Clinical Endocrinology and Metabolism 2004

Example 22

Example of a Synergistic Effect of GnRH Antagonist Treatment with Famprydine, a Multiple Sclerosis Drug Patient History
  58 year old female with multiple sclerosis with disease duration of 8 years.
  Fulfilled the McDonald 2010 criteria for the diagnosis of multiple sclerosis (MS).
Experimental Treatment and Assessment of Response
  For the last 2.5 years, she had been taking stable concomitant Famprydine, a potassium channel blocker, for symptomatic treatment for MS. Her MS disease activity had been increasing gradually over these 2.5 years, requiring her to use crutches, and eventually a walker. In December 2014, she started experimental treatment with Degarelix. She received a loading dose of 240 mg sc 8 Dec. 2014 and 80 mg sc every two weeks thereafter.
  By 6 weeks she had responded surprisingly well (refer to previous example with detailed assessment endpoints).

One of the most objective endpoints is the 'timed 25 meter walk'.

At baseline, she used 16.7 seconds.
By 6 weeks she used 15.2 seconds.
By 2 months 14.0 seconds.
By 4 months 11.9 seconds.
By 5 months 11.8 seconds (30 Mar. 2015)
She was able to use crutches more frequently and physiotherapy exercises were completed more easily. She describes in an interview that for the first time she could easily complete certain exercises with her under extremities that she had previously never been able to do during her physiotherapy visits.
Due to this effect, she decided to discontinue her long term stable Famprydine medication on 5 Apr. 2015. This had a detrimental effect on her timed walk test which increased from 11.9 seconds to 14.0 seconds on the 29 Apr. 2015.
In May 2015 we reintroduced Famprydine.
It is unlikely that the benefits observed were purely due to Famprydine as she had used stable Famprydine for 2.5 years without experiencing such improvements earlier (as confirmed in her interview as well).

This example demonstrates that the combination of GnRH antagonist treatment with a MS drug, such as Famprydine, improved signs and symptoms in multiple sclerosis. This improvement in progressive MS is likely to also be observed in the relapsing-remitting type of MS. This is because the relapsing-remitting type gives similar signs and symptoms as the progressive type to patients over time.

Example 23

Example of Intra-Articular GnRH Inhibiting Treatment in a Patient with Osteoarthritis Patient History
 78 year old male with osteoarthritis of both knees diagnosed by x-ray 10 years ago
 Has had synovitis secondary to osteoarthritis in both knees for the last month, confirmed by synovitis on ultrasound.
Experimental Treatment
 In order to treat the secondary inflammation as a result of his knee osteoarthritis, he is offered intra-articular GnRH antagonist treatment, for example Cetrorelix lmg injected into both knees. Subcutaneous Cetrorelix for injection can be used.
Assessment of Response
 Before and 2 week post injection ultrasound images are taken to show a decrease in synovitis in the knee joint.
 This example demonstrates how a drug that lowers the effects of GnRH, such as Cetrorelix, may be administered intra-articularly to treat inflammation.

Example 24

Example of a Patient Using Spiroindoline Derivatives as Gonadotropin-Releasing Hormone Receptor Antagonists Patient History
 60 year old female with seropositive rheumatoid arthritis with disease duration of 20 years.
 Fulfills ACR 2010 classification criteria for rheumatoid arthritis.
Experimental Treatment
 Treated with a spiroindoline derivative as a GnRH antagonist orally 200 mg daily for 12 weeks.
Assessment of Response at 4 Months
 Disease activity score (DAS) is reduced with over 0.6 units.
 A DAS reduction of 0.6 units is defined as a clinical response to treatment (1).
 This example demonstrates how spiroindoline derivatives as GnRH antagonists, can improve signs and symptoms in a patient with rheumatoid arthritis shown with international response criteria.

Reference for Example 24

1. Van Gestel A M, et al. Development and validation of the European League Against Rheumatism response criteria for rheumatoid arthritis. Arthritis Rheum 1996; 39: 34.40.

Example 25

Example of a Patient with Tendonitis Treated with a GnRH Antagonist Injection

Patient History
 61 year old male diagnosed with tendonitis of the elbow with ultrasound confirming tendonitis.
Experimental Treatment
 Treated with an injection of GnRH antagonist, Ganirelix 1.5 mg, around the affected tendon.
Assessment of Response
 Before and 2 week post injection ultrasound images are taken to show a decrease in tendonitis of the elbow.
 This example demonstrates how a drug that lowers the effects of GnRH, such as Ganirelix, may be administered around tendons to treat inflammation. Such injections may be administered over long-term, for example every 3 months to maintain optimal effect.

Example 26

Example of a Patient with Psoriatic Arthritis Treated with the Oral GnRH Antagonist ASP1707

Patient History
 48 year old male with psoriatic arthritis
 Fulfills CASPAR 2006 classification criteria for psoriatic arthritis.
Experimental Treatment
 Is offered experimental GnRH antagonist therapy, ASP1707 3 mg daily for 12 weeks.
Assessment of Response at 4 Months
 Disease activity score (DAS) is reduced with over 0.6 units.
 A DAS reduction of 0.6 units can be defined as a clinical response to treatment (1).
 This example demonstrates how ASP1707, a GnRH antagonist, improves signs and symptoms in a patient with rheumatoid arthritis shown with international response criteria.

Reference for Example 26

1. Mease P J, et al. Psoriatic arthritis assessment tools in clinical trials. Ann Rheum Dis 2005; (Suppl II):ii49-ii54. doi: 10.1136/ard.2004.034165.

Example 27

We analysed peripheral GnRH levels in patients with various autoimmune diseases using ELISA. We found that patients with autoimmune diseases had higher levels of peripheral GnRH than healthy controls. We also found that GnRH antagonist treatment over a period of months reduced peripheral GnRH levels to some extent in patients with various autoimmune diseases. Due to the nature of ELISA assays, the concentration in pg/mL should not necessarily be regarded as absolute, and may be interpreted as relative.

RA Pt A Baseline GnRH 394 pg/mL, after 3months of Degarelix with loading dose 240 mg, and maintenance doses 80 mg every 2 weeks, GnRH 359 pg/mL. During this period CRP was reduced from 142 mg/L to 54 mg/L and disease activity reduced significantly from 8.6 to 4.2 in DAS score. Multiple Sclerosis Patient B Baseline GnRH 318 pg/mL, reduced to 210 pg/mL after 1 month of GnRH antagonist treatment; Degarelix 240 mg loading dose and 80 mg every 2 weeks for maintenance. During that month/6 weeks her general function had improved, for example MSIS-29 had reduced from 121 to 110. Psoriasis Patient C Baseline GnRH 300 pg/mL reduced to 274 pg/mL after 3 months Degarelix treatment with loading dose 240 mg, and maintenance doses of 80 mg every 2 weeks. During that period his PASI score reduced by more than 20%. Healthy control 1 baseline GnRH 162 pg/mL, healthy control 2 baseline GnRH 120 pg/mL, healthy control 3 baseline GnRH 153 pg/mL.

This example shows that patients with inflammatory diseases may have higher peripheral GnRH levels than healthy controls, and this example shows how assessing peripheral levels of GnRH can be used to generally used to diagnose inflammatory diseases and evaluate treatment effect/prognostic evaluation.

Example 28

A Fusion GnRH Antagonist Compound

Functionalization of the PEG polymer at one or both terminal is carried out. The chemically active or activated derivatives of the PEG polymer are prepared to attach the PEG to the desired molecule, the GnRH antagonist or drug to lower GnRH activity. The overall PEGylation process is either a solution phase batch process or an on-column fed-batch process. During the simple and commonly adopted batch process reagents are mixed together in a suitable buffer solution, preferably at a temperature between 4 and 6° C. The choice of the suitable functional group for the PEG derivative is based on the type of available reactive group on the molecule that is coupled to the PEG. For proteins, typical reactive amino acids include lysine, cysteine, histidine, arginine, aspartic acid, glutamic acid, serine, threonine, tyrosine. The N-terminal amino group and the C-terminal carboxylic acid can also be used as a site specific site by conjugation with aldehyde functional polymers. For first generation PEG derivatives the PEG polymer reacts with a group that is reactive with hydroxyl groups, typically anhydrides, acid chlorides, chloroformates and carbonates. For second generation PEG derivatives, more efficient functional groups such as aldehyde, esters, amides etc. is made available for conjugation. Heterobifunctional PEGs are very useful in linking two entities, where a hydrophilic, flexible and biocompatible spacer is needed. Preferred end groups for heterobifunctional PEGs are maleimide, vinyl sulfones, pyridyl disulfide, amine, carboxylic acids and NHS esters. Third generation pegylation agents, where the shape of the polymer has been branched, Y shaped or comb shaped are available which show reduced viscosity and lack of organ accumulation. These compounds are tested in animal studies, showing that they do not cross the blood brain barrier due to their physically large size. Some of these compounds can have extended half lives. They do not act upon the pituitary GnRH receptors. They are shown to only act upon peripheral GnRH receptors, avoiding side effects of decreased oestrogen and testosterone in females and males respectively. They are administered through several routes, including oral routes. This enables long term administration for years, and in some examples maintenance of the menstrual cycle in premenopausal women.

Example 29

A Monoclonal Antibody Compound

Mice are immunized to stimulate anti-GnRH antibody production. Antibody forming cells are isolated from the spleen. Tumor cells are grown in tissue culture. Antibody-forming cells that are isolated from the spleen are fused with cultivated tumor cells to form hybridomas. Hybridomas are screened for antibody production. Antibody producing hybridomas are cloned. Monoclonal antibodies are isolated for cultivation. The monoclonal antibody works by binding with high affinity to peripheral GnRH, preventing the binding of GnRH to its receptor. The antibody is a large molecule that is unable to pass the BBB therefore central GnRH receptors remain unaffected, thereby the reproductive hypothalamic pituitary gonadal axis is unaffected.

Example 30

Example Treatment Using the Oral GnRH Antagonist Relugolix

Patient History
   38 year old male with spondyloarthritis with disease duration of 5 years.

Experimental Treatment
   Is offered experimental GnRH antagonist therapy, Relugolix 400 mg daily for 12 weeks.

Assessment of Response at 4 Months
   Disease activity in ankylosing spondylitis/spondyloarthritis is measured by the BASDAI score. His BASDAI is 5 at baseline. It is 1.2, in remission, at 12 weeks.
   This example demonstrates that Relugolix, a GnRH antagonist, improves signs and symptoms in a patient with spondyloarthritis.

Example 31

Example Treatment Using the Oral GnRH Antagonist Elagolix

Patient History
   38 year old female with systemic sclerosis (scleroderma) with disease duration of 1 year.

Experimental Treatment
   Is offered experimental GnRH antagonist therapy, Elagolix 600 mg daily for 12 weeks.

Assessment of Response
   Digital ulcers decrease from 6 to 2
   Health assessment questionnaire improves from 2.0 to 1.0

This example demonstrates that Elagolix, a GnRH antagonist, improves signs and symptoms in a patient with systemic sclerosis (scleroderma).

Example 32

Example Treatment Using the Oral GnRH Antagonist Asp1707 to Reduce Cancer Related Inflammation Inflammation and cancer are linked inextricably. Inflammation has been described as the 7$^{th}$ hallmark of cancer. The majority of cancer related symptoms are associated with inflammation.

Patient History
  68 year old male with colon cancer with disease duration of 1 year. Suffers from signs and symptoms of cancer related inflammation, such as pain, anorexia, and fatigue.

Experimental Treatment
  Is offered experimental treatment, ASP1707 8 mg daily, to reduce signs and symptoms associated with cancer related inflammation Assessment of Response
  At 3 months patient experiences reduced signs and symptoms of cancer related inflammation, such as pain, anorexia and fatigue.
  At 3 months, his high baseline CRP of 40 mg/L is decreased to 12 mg/L.

This example demonstrates that ASP 1707, a GnRH antagonist, improves signs and symptoms in a patient with cancer related inflammation.

Example 33

Example of a GnRH Antagonist Treatment for Colitis

Patient History
  55 year old female with ulcerative colitis for the past 10 years Experimental Treatment
  Is offered Ganirelix 2 mg daily for 6months Assessment of Response
  By 6 months she experiences clinical remission with a partial Mayo score reduction from 3 to 0.

This example demonstrates how a GnRH antagonist may be given to treat an inflammatory bowel disease.

Example 34

Figure 14:
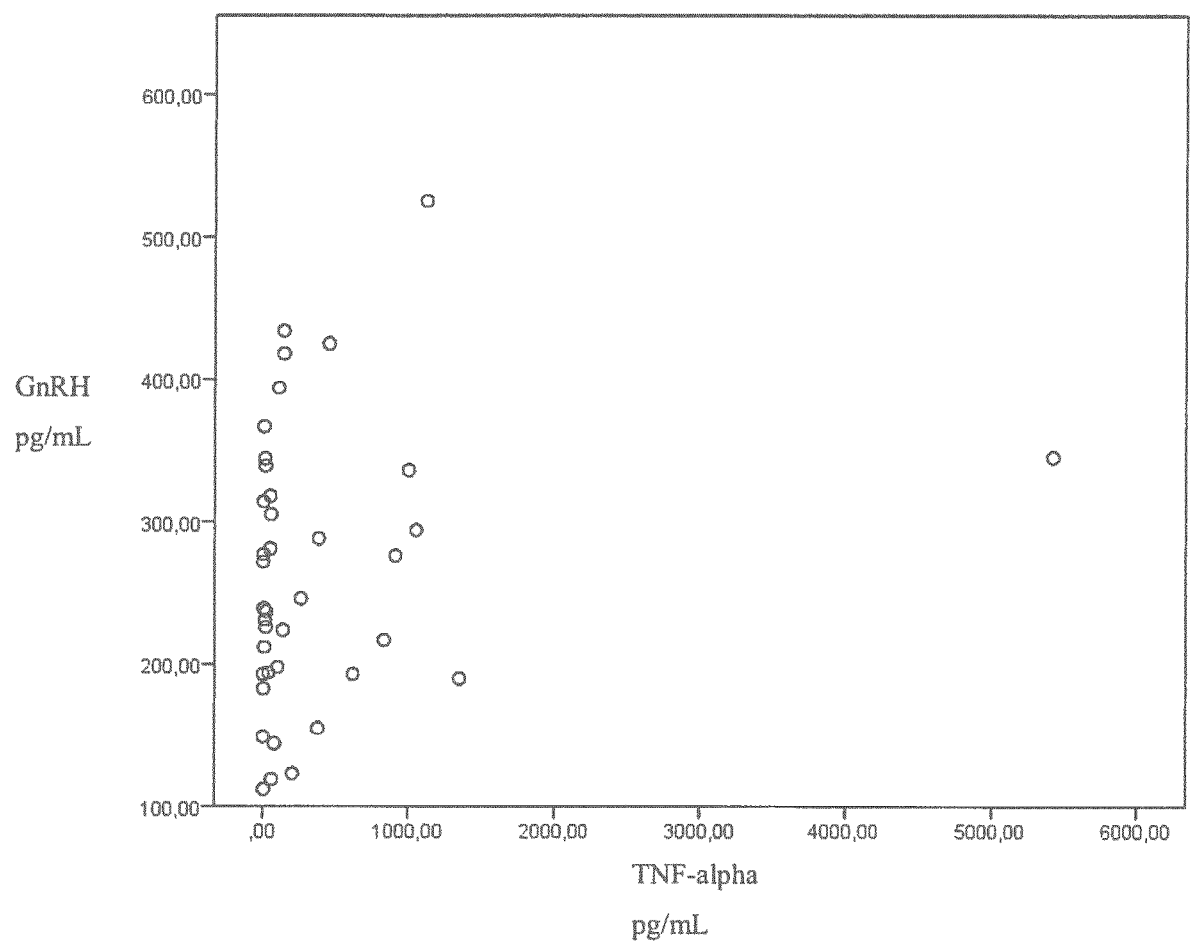
FIG. 14 shows a graph depicting the association of GnRH and TNF-alpha in the periphery of patients with rheumatoid arthritis.

The association of GnRH and TNF-alpha in the periphery of patients with rheumatoid arthritis was assessed and the results are shown in FIG. 14.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology, in vitro fertilization, development, or related fields are intended to be within the scope of the following claims.

The invention claimed is:

1. A method of treating rheumatoid arthritis in a subject, said method comprising:
  administering degarelix to said subject, wherein said administration is long-term for a period of at least 3 months.

2. The method of claim 1, further comprising the step of administering one or more additional active agents.

3. The method of claim 2, wherein:
  said additional active agent is useful for the treatment of inflammation and/or an autoimmune disease.

4. The method of claim 2, wherein said additional active agent is selected from the group consisting of: a sex hormone, an agent useful in sex hormone substitution therapy, an anti-rheumatic agent, a non-steroidal anti-inflammatory drug (NSAID), a biologic agent, an analgesic, and a glucocorticoid.

5. The method of claim 4, wherein said additional active agent is selected from the group consisting of: oestrogen, testosterone, luteinizing hormone (LH), follicle-stimulating hormone (FSH), and methotrexate.

6. The method of claim 1, wherein degarelix is administered to said subject:
  (a) for at least six months;
  (b) daily, weekly, or monthly; and/or
  (c) as a single loading dose followed by a lower maintenance dose.

7. The method of claim 1, wherein:
  the degarelix is administered to said subject at 2 to 4 week intervals.

8. The method of claim 7, wherein degarelix is administered to said subject at a dosage of 10-1000 mg.

9. The method of claim 1, wherein degarelix is administered to said subject at a dosage which is higher than the dosage used in the treatment of prostate cancer.

10. The method of claim 1, wherein degarelix is administered to said subject at a dosage which is at least double the licensed dosage.

11. The method of claim 1, wherein degarelix is administered to said subject at a dosage of 10-1000 mg weekly, every 2 to 4 weeks, monthly, or at 2 to 6 month intervals.

* * * * *